United States Patent [19]
Smith et al.

[11] Patent Number: 5,972,624
[45] Date of Patent: Oct. 26, 1999

[54] METHOD OF IDENTIFYING LIGANDS WHICH BIND RECOMBINANT GALANIN RECEPTOR (GALR2)

[75] Inventors: Kelli E. Smith, Wayne; Christophe P. G. Gerald, Ridgewood; Richard L. Weinshank, Teaneck; David Linemeyer, Westfield; Theresa Branchek, Teaneck; Carlos Forray, Paramus, all of N.J.

[73] Assignee: Synaptic Pharmaceutical Corporation, Paramus, N.J.

[21] Appl. No.: 08/626,685

[22] Filed: Apr. 1, 1996

Related U.S. Application Data

[63] Continuation-in-part of application No. 08/590,494, Jan. 24, 1996, abandoned.

[51] Int. Cl.$^6$ .......................... G01N 33/53; G01N 33/566
[52] U.S. Cl. ............................................ 435/7.2; 435/69.1
[58] Field of Search ................................... 435/7.2, 69.1, 435/325; 530/350; 536/23.1

[56] References Cited

U.S. PATENT DOCUMENTS

| | | | |
|---|---|---|---|
| 5,290,808 | 3/1994 | Sofia et al. | 514/483 |
| 5,436,128 | 7/1995 | Harpold et al. | 435/6 |
| 5,436,155 | 7/1995 | Bell et al. | 435/252.3 |
| 5,462,856 | 10/1995 | Lerner et al. | 435/7.21 |
| 5,567,714 | 10/1996 | Bruns et al. | 514/324 |
| 5,576,296 | 11/1996 | Bartfai et al. | 514/13 |

FOREIGN PATENT DOCUMENTS

| | | |
|---|---|---|
| 0514361 | 11/1992 | European Pat. Off. . |
| 0711830 | 5/1996 | European Pat. Off. . |
| 9212997 | 8/1992 | WIPO . |
| 9215015 | 9/1992 | WIPO . |
| 9215681 | 9/1992 | WIPO . |
| 9522608 | 8/1995 | WIPO . |
| 9746681 | 12/1997 | WIPO . |

OTHER PUBLICATIONS

Marieb, E.N. (1992) Human Anatomy and Physiology, $2^{nd}$ Edition, Benjamin/Cummings Publishing Company, Inc., Redwood City, California, pp. 547–551, 1992.

Ahmad, A., et al. "Identification And Molecular Cloning Of A Novel Galanin Receptor (GALR–2) In Rat Sensory Neurons" *Soc. Neurosci. Abstr.* (1996) 22:3 1682, Abstract 661.10.

Ahmad, S., et al. "Molecular Cloning Of A Novel Widely Distributed Galanin Receptor Subtype (GALR2)" *International Association for the Study of Pain* (IASP Press) (1996) Abstract No. 81: 134.

O'Donnell, D., et al. "Neuroanatomical Distribution Of A Novel Rat Galanin Receptor Subtype" *Soc. Neurosci. Abstr.* (1996) 22(2): 1304, Abstract 517.9.

Bouvier, M., et al. "Dynamic Palmitoylation of G–Protein–Coupled Receptors in Eukaryotic Cells" *Methods in Enzymology* (1995) 250: 300–314.

Parker, et al. "Cloning and Characterization of the Rat GALR1 Galanin Receptor From Rin14B Insulinoma Cells" *Molecular Brain Research* (1995) 34:2 179–189.

Reerk, et al. "'Homology ' In Proteins And Nucleic Acids: A Terminology Muddle And A Way Out Of It" *Cell* (1987) 50: 667; and.

Wallace, et al. *Methods In Enzymology* 152: 432–442.

Bartfai, T. et al. PNAS (USA). 90:11287–11291, (1993).

Burgevin, M.–C. et al. J. Molec. Neurosci. 6:33–41, (1995).

Chen, Y. et al. PNAS (USA). 90:3845–3849, (1993).

Deecher, D.C. et al. J. Pharmacol. Exp. Ther. 275:720–727, (1995).

Gu, Z.–F. et al. J. Pharmacol. Exp. Ther. 272:371–378, (1995).

Gustafson, E. et al. Neuroreport. 7:953–957, (1996).

Habert–Ortoli, E. et al. PNAS (USA). 91:9780–9783, (1994).

Heuillet, E. et al. Eur. J. Pharmacol. 269:139–147, (1994).

Kahl, U. and Bartfai, T. Galanin Receptors. 8(7):404–410, (1995).

Kask, K. et al. EMBO J. 15(2):236–244, (1996).

Lorimer, D.D. and Benya, R.V. Biochem. Biophys. Res. Comm. 222:379–386, (1996).

Lorinet, A.–M. et al. Eur. J. Pharmacol. 269:59–64, (1994).

Valkna, A. et al. Neurosci. Lett. 187:75–78, (1994).

Walli, R. et al. J. Mol. Endocrinol. 13:347–356, (1994).

Wynick, D. et al. PNAS (USA). 90:4231–4235, (1993).

Xu, X.–J. et al. Br. J. Pharmacol. 116:2076–2080, (1995).

*Primary Examiner*—Lila Feisee
*Assistant Examiner*—Michael Pak
*Attorney, Agent, or Firm*—John P. White; Cooper & Dunham LLP

[57] ABSTRACT

This invention provides an isolated nucleic acid encoding a mammalian galanin receptor, an isolated galanin receptor protein, vectors comprising an isolated nucleic acid encoding a galanin receptor, cells comprising such vectors, antibodies directed to the galanin receptor, nucleic acid probes useful for detecting nucleic acid encoding galanin receptors, antisense oligonucleotides complementary to unique sequences of a nucleic acid encoding a galanin receptor, nonhuman transgenic animals which express DNA encoding a normal or a mutant galanin receptor, as well as methods of determining binding of compounds to the galanin receptor.

6 Claims, 16 Drawing Sheets

FIGURE 1

```
   1  CAAGACCCCGGACAGCTGCGGGAGCGGCGTCCACTTTGGTGATACCATGAATGGCTCCGGC      60
  61  AGCCAGGGCGGGAGAACGAGCCAGGAAGGCGGTAGCGGCGGCTGGCAGCCTGAGGCG       120
 121  GTCCTTGTACCCCTATTTTCGCGCTCATCTTCCTGTGGCACCGTGGGCAACGCGCTG       180
 181  GTGCTGGCCGGTGCTGCTGCGCGGCCAGGCGGTCAGCGGTCAGCCAGCCAACCTGTTCATCCTC       240
 241  AACCTGGGCGTGGCCGACCTGGGTGTGTTCGGCTGTGCTCATCCTGCTGCCAAGGCTGTTCATTTCCTCATC       300
 301  TACACCCTGGACGACTGGGCCAGCAGCTTCACGCGCCTTCACGCGCTTCCCCTGGACAGGTATCTG       360
 361  TTTCTCACTATGCACGCCAGCAGCTTCACGCGCTGCACACCTCCCCGAGAGTGCGCTACCTGAAACGCGCTGGCCGCC       420
 421  GCCATCCGCTACCCGCTGGGGGCTAGCACCTCCCCGAGAGTGCTCTTCTCCGGCCCTACCTGAGCGCACCTACCGT       480
 481  ATCGGCTCATCTGGGCCAACCTGCACCTTTCGTCTTCGCGCTACCTGCCAGTGCTGCTAGTCCTCAGTCTG       540
 541  CAGTCGCAGCTGGCCAGCCTCTGCACCCTACCCCTGCGCGCTACCCTCTGGCCACAGTGACCCGGTGACTGCAGGCTCA       600
 601  GCCATGGACCTCTGCAGCTGCACCCTGCGCGCTACCCTCTGGCCACAGTGACCCGGTGACTGCAGGCTCA       660
 661  ACCTATGCGCGTACCCCTGCCCGCTACCCTCTGGCGCACAGTGACCCGGTGACTGCAGGCTCA       720
 721  GGTTCCCAGCGCGCCAAACGCGCCCCACCACGCAAGGTGACACGGATGATCCTCTGCGGTGTTGGTGCTTTTC       780
 781  TGCCTCTGTTGGATGCCCCACCACGCTTATCCTCACGCGCTTATCCTTTCACACACACAGCATTTCCGTTCCTATGCCAACTCC       840
 841  CTCACGCGTGCCACTTACGCGTTTACGCGCCTCTGGTCTCCCAAGCATTTCCGTTCCTATGCCAACTCC       900
 901  TGTGTCAACCCCATCGTTTGCGCCCTGCCCCGAGGCGAGCTTCGGGCCGAGTGAGCTTCCGCAAA       960
 961  ATCTGCGCGGCCTGGGAACCATAGTGGCAGCATGCTTGAACAGGAATCCACAGACCTGACACAGGTG      1020
1021  GCGCCTGGGAACCATAGTGGCAGCATGCTTGAACAGGAATCCACAGACCTGACACAGGTG      1080
1081  AGCGAGGCAGCCCGGGCCCCCTTGTCCCACCACGCACTCCCAACTGCACAGCCTGAGT      1140
1141  AGAACCCTGATCCCGGGCTTGTTAAAGGACCAAAGGGCATCTAACAGCTTCTAG              1193
```

FIGURE 2

|  | 20 | 40 | 60 | 80 | 100 | 120 | 140 | 160 | 180 | 200 | 220 | 240 | 260 | 280 | 300 | 320 | 340 | 360 | 372 |
|---|---|---|---|---|---|---|---|---|---|---|---|---|---|---|---|---|---|---|---|
| | G | T | T | P | A | S | R | Y | S | V | P | H | W | V | R | G | T | N | |
| | G | G | T | V | K | V | P | P | W | P | D | I | V | L | F | S | P | | |
| | S | V | S | C | A | T | G | A | L | V | I | C | H | H | A | E | L | | |
| | G | L | V | C | L | A | R | S | P | L | T | M | L | S | K | R | Q | A | |
| | G | F | A | L | L | L | F | H | Y | R | R | I | L | S | R | E | P | | |
| | E | I | Q | H | S | T | E | L | C | S | W | T | L | I | V | P | L | P | |
| | Q | L | G | F | G | R | L | V | F | L | V | A | R | L | A | M | P | | |
| | S | A | G | C | F | S | S | A | T | V | Y | K | H | L | A | P | S | V | |
| | T | F | R | L | V | S | H | L | F | R | R | H | A | Y | R | G | L | C | |
| | N | F | L | D | W | A | L | G | N | T | L | K | P | Y | V | L | S | P | A |
| | A | L | L | A | D | H | P | W | A | C | T | A | M | T | L | H | G | P | P |
| | A | P | V | D | M | Y | I | L | L | R | R | W | A | P | G | N | A | D | |
| | G | V | A | G | L | T | R | L | Q | D | A | Q | C | R | N | A | G | A | L |
| | Q | L | L | L | T | L | I | G | S | M | Y | S | L | V | C | A | P | E | T |
| | S | V | V | N | Y | F | A | I | Q | A | T | G | C | L | C | I | A | S | R |
| | G | A | L | L | I | L | A | R | R | L | S | F | P | S | K | L | V | S | |
| | S | E | A | I | T | L | Y | A | Y | R | S | G | L | F | N | R | I | Q | S |
| | G | P | N | F | A | F | R | L | Y | R | L | A | V | R | A | F | S | T | A |
| | N | Q | G | L | Q | H | D | A | S | P | V | T | A | G | Y | G | V | L | T |
| | M | W | V | N | F | V | L | N | L | A | L | V | V | F | S | K | R | D | C |
| 1 | 21 | 41 | 61 | 81 | 101 | 121 | 141 | 161 | 181 | 201 | 221 | 241 | 261 | 281 | 301 | 321 | 341 | 361 | |

FIGURE 3C

```
414   GTGAGTGAACATCGGAGAACTATTGTATCTGAGATAGGGGCTTGGGCTGGAGTCACTACA   473
474   CAGGGGATCCAGAAGGCATGAGCAGAGAATGGGCGAGAACACTGAAATTACAAAGTGCCTG   533
534   AGGCCCGTGAAACGCCAAGGGGGAGGGAGATTAAGACTCAGTGACTGAGAGTGTCTAAGTCG   593
594   ATGGGAGAAATCGGTCTCTGGGGTCCTCGCATTATTACTGCTTGAGTTAAATGTCTCTG   653
654   TGAAACATTGCAGTTCTCAGGCCAGAGTTGGCAGGAAAAGTAACTCGCCAGTGTTCAGAT   713
714   GCTGTTTGAGAGCTGCAGAGAAGCATCTGCTTCTTAGCACCAAGCTCAGCACCTGGGGCG   773
774   TTGTCCGGCCTTAGGCTTAGGACTGGGCTGTGTGCTTAAGACCCATGCTCAAGTCC   833
834   AACGGAGTGTAAGCGAGGGCTCCTAGCTGACACCCAGAGCCCTCCAGGCCAAGGCTCCCC   893
894   TCACCGAGATGCCAGCCGGTTTTATGCTCCTTCCATAGGTAAAGGACCCAGAGAAACAT   953
954   CCAGTATGCCCGGAGGGATCTTGACTGGAAAAGACTGAATCCTGGTCTGGTGACCTTAGT   1013
1014  TCCCTGCCCTTTCACATCACTTGGACATTCCCACAGAAGAGCGGTGAAGAGGCGGTGGTC   1073
1074  CTTATTCTCCTCTGGTTTCCACTGAGTGCCAACATGTGCCGTCCTGAGTACGCTGGAGGAC   1133
1134  TCACAAAATTTCAGCTTTCTTTAGGAGTTTCCTTGCTGTAGTTTGACCCAAGTCTTCTCC   1193
1194  AGGTTTCTGTCAGAACCTCAGGCATGAGGGGATCTGCCTCCCCGTTGTCACCAGAGGAT   1253
1254  AACAATCACTGCCCCAGAAATCCAGACAGATTCTACAACTTTTAGTCTTCGGTGTTTG   1313
1314  GGGGTGCCCTTCACGTGGAGTAGGTCGGTGCCACATTCCCAGGAGTGACAATAGCCTA   1373
1374  GCAGTGAATCCTCTCGCTTAGCTGATGCCCCCACTGTCCCCACAG                1420
```

METHOD OF IDENTIFYING LIGANDS WHICH BIND RECOMBINANT GALANIN RECEPTOR (GALR2)

This application is a continuation-in-part of U.S. Ser. No. 08/590,494, filed Jan. 24, 1996, now abandoned the contents of which are hereby incorporated by reference.

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the sequence listing and the claims.

The neuropeptide galanin and its receptors hold great promise as targets for the development of novel therapeutic agents. Galanin is widely distributed throughout the peripheral and central nervous systems and is associated with the regulation of processes such as somatosensory transmission, smooth muscle contractility, hormone release, and feeding (for review, see Bartfai et al., 1993). In the periphery galanin is found in the adrenal medulla, uterus, gastrointestinal tract, dorsal root ganglia (DRG), and sympathetic neurons. Galanin released from sympathetic nerve terminals in the pancreas is a potent regulator of insulin release in several species (Ahrén and Lindskog, 1992; Boyle et al., 1994), suggesting a potential role for galanin in the etiology or treatment of diabetes. High levels of galanin are observed in human and rat anterior pituitary where galanin mRNA levels are potently upregulated by estrogen (Vrontakis et al., 1987; Kaplan et al., 1988). The presence of galanin in the hypothalamic-pituitary-adrenal axis coupled with its potent hormonal effects has led to the suggestion that galanin may play an integral role in the hormonal response to stress (Bartfai et al., 1993).

Within the CNS galanin-containing cell bodies are found in the hypothalamus, hippocampus, amygdala, basal forebrain, brainstem nuclei, and spinal cord, with highest concentrations of galanin in the hypothalamus and pituitary (Skofitsch and Jacobowitz, 1985; Bennet et al., 1991; Merchenthaler et al., 1993). The distribution of galanin receptors in the CNS generally complements that of galanin peptide, with high levels of galanin binding observed in the hypothalamus, amygdala, hippocampus, brainstem and dorsal spinal cord (Skofitsch et al., 1986; Merchenthaler et al., 1993; see Bartfai et al., 1993). Accordingly, agents modulating the activity of galanin receptors would have multiple potential therapeutic applications in the CNS. One of the most important of these is the regulation of food intake. Galanin injected into the paraventricular nucleus (PVN) of the hypothalamus stimulates feeding in satiated rats (Kyrkouli et al., 1990), an effect which is blocked by the peptide galanin antagonist M40 (Crawley et al., 1993). In freely feeding rats, PVN injection of galanin preferentially stimulates fat-preferring feeding (Tempel et al., 1988); importantly, the galanin antagonist M40 administered alone decreases overall fat intake (Leibowitz and Kim, 1992). These data indicate that specific receptors in the hypothalamus mediate the effects of galanin on feeding behavior, and further suggest that agents acting at hypothalamic galanin receptors may be therapeutically useful in the treatment of human eating disorders.

Galanin receptors elsewhere in the CNS may also serve as therapeutic targets. In the spinal cord galanin is released from the terminals of sensory neurons as well as spinal interneurons and appears to play a role in the regulation of pain threshold (Wiesenfeld-Hallin et al., 1992). Intrathecal galanin potentiates the anti-nociceptive effects of morphine in rats and produces analgesia when administered alone (Wiesenfeld-Hallin et al., 1993; Post et al., 1988); galanin receptor agonists may therefore be useful as analgesic agents in the spinal cord. Galanin may also play a role in the development of Alzheimer's disease. In the hippocampus galanin inhibits both the release (Fisone et al., 1987) and efficacy (Palazzi et al., 1988) of acetylcholine, causing an impairment of cognitive functions (Sundström et al., 1988). Autopsy samples from humans afflicted with Alzheimer's disease reveal a galaninergic hyperinnervation of the nucleus basalis (Chan-Palay, 1988), suggesting a role for galanin in the impaired cognition characterizing Alzheimer's disease. Together these data suggest that a galanin antagonist may be effective in ameliorating the symptoms of Alzheimer's disease (see Crawley, 1993). This hypothesis is supported by the report that intraventricular administration of the peptide galanin antagonist M35 improves cognitive performance in rats (Ogren et al., 1992). Human galanin receptors thus provide targets for therapeutic intervention in multiple CNS disorders.

High-affinity galanin binding sites have been characterized in brain, spinal cord, pancreatic islets and cell lines, and gastrointestinal smooth muscle in several mammalian species, and all show similar affinity for $^{125}$I-porcine galanin (~0.5–1 nM). Nevertheless, recent in vitro and in vivo pharmacological studies in which fragments and analogues of galanin were used suggest the existence of multiple galanin receptor subtypes. For example, a galanin binding site in guinea pig stomach has been reported that exhibits high affinity for porcine galanin (3-29) (Gu, et al. 1995), which is inactive at CNS galanin receptors. The chimeric galanin analogue M15 (galantide) acts as antagonist at CNS galanin receptors (Bartfai et al., 1991) but as a full agonist in gastrointestinal smooth muscle (Gu et al., 1993). Similarly, the galanin-receptor ligand M40 acts as a weak agonist in RINm5F insulinoma cells and a full antagonist in brain (Bartfai et al, 1993a). The pharmacological profile of galanin receptors in RINm5F cells can be further distinguished from those in brain by the differential affinities of [D-Tyr$^2$]- and [D-Phe$^2$]-galanin analogues (Lagny-Pourmir et al., 1989). The chimeric galanin analogue M35 displaces $^{125}$I-galanin binding to RINm5F membranes in a biphasic manner, suggesting the presence of multiple galanin receptor subtypes, in this cell line (Gregersen et al., 1993).

Multiple galanin receptor subtypes may also co-exist within the CNS. Galanin receptors in the dorsal hippocampus exhibit high affinity for Gal (1-15) but not for Gal (1-29) (Hedlund et al., 1992), suggesting that endogenous proteolytic processing may release bioactive fragments of galanin to act at distinct receptors. The rat pituitary exhibits high-affinity binding for $^{125}$I-Bolton and Hunter (N-terminus)-labeled galanin (1-29) but not for [$^{125}$I]Tyr$^{26}$-porcine galanin (Wynick et al., 1993), suggesting that the pituitary galanin receptor is a C-terminus-preferring subtype. Spinal cord galanin binding sites, while similar to those in brain, show an affinity for the chimeric peptide antagonist M35 intermediate between the brain and smooth muscle (Bartfai et al., 1991), raising the possibility of further heterogeneity.

A galanin receptor cDNA was recently isolated by expression cloning from a human Bowes melanoma cell line (Habert-Ortoli et al., 1994). The pharmacological profile exhibited by this receptor is similar to that observed in brain and pancreas, and on that basis the receptor has been termed GALR1. The cloned human GALR1 receptor binds native human, porcine and rat galanin with ~1 nM affinity ($K_i$ vs. $^{125}$I-galanin) and porcine galanin 1-16 at a slightly lower affinity (~5 nM). Porcine galanin 3-29 does not bind to the receptor. The GALR1 receptor appears to couple to inhibition of adenylate cyclase, with half-maximal inhibition of forskolin-stimulated cAMP production by 1 nM galanin, and maximal inhibition occurring at about 1 $\mu$M.

Recently the rat homologue of GALR1 was cloned from the RIN14B pancreatic cell line (Burgevin, et al., (1995), Parker et al., 1996; Smith et al., in preparation). The pharmacologic data reported to date do not suggest substantial differences between the pharmacologic properties of the rat and human GALR1 receptors. Localization studies reveal GALR1 mRNA in rat hypothalamus, ventral hippocampus, brainstem, and spinal cord (Gustafson et al., in press), regions consistent with roles for galanin in feeding, cognition, and pain transmission. However, GALR1 appears to be distinct from the pituitary and hippocampal receptor subtypes described above.

The indication of multiple galanin receptor subtypes within the brain underscores the importance of defining galanin receptor heterogeneity at the molecular level in order to develop specific therapeutic agents for CNS disorders. Pharmacological tools capable of distinguishing galanin receptor subtypes in tissue preparations are only beginning to appear. Several high-affinity peptide-based galanin antagonists have been developed and are proving useful in probing the functions of galanin receptors (see Bartfai et al., 1993), but their peptide character precludes practical use as therapeutic agents. In light of galanin's multiple neuroendocrine roles, therapeutic agents targeting a specific disorder must be selective for the appropriate receptor subtype to minimize side effects.

Accordingly, applicants have endeavored to clone the entire family of galanin receptors for use in target-based drug design programs. The identification of non-peptide agents acting selectively only at specific galanin receptors will be greatly facilitated by the cloning, expression, and characterization of the galanin receptor family.

Applicants now report the isolation by expression cloning of a novel galanin receptor from a rat hypothalamic cDNA library, as well as its pharmacological characterization in a heterologous expression system. The data provided demonstrate for the first time the existence of a new galanin receptor subtype, from now on referred to as the GALR2 subtype, or simply, "GALR2." This discovery provides a novel approach, through the use of heterologous expression systems, to develop subtype selective, high-affinity non-peptide compounds that could serve as therapeutic agents for eating disorders, diabetes, pain, depression, ischemia, and Alzheimer's disease. The presence of both GALR1 and GALR2 in rat hypothalamus suggests that multiple galanin receptors may be involved in the regulation of feeding.

Pathophysiological disorders proposed to be linked to galanin receptor activation include eating disorders, diabetes, pain, depression, ischemia, Alzheimer's disease and reproductive disorders. Accordingly, treatment of such disorders may be effected by the administration of GALR2 receptor-selective compounds. The localization of GALR2 receptors in other parts of the rat brain suggests that GALR2 receptors may play a role in cognition, analgesia, sensory processing (olfactory, visual), processing of visceral information, motor coordination, modulation of dopaminergic activity, neuroendocrine function, sleep disorders, migraine, and anxiety.

SUMMARY OF THE INVENTION

This invention provides an isolated nucleic acid encoding a mammalian GALR2 galanin receptor. This invention also provides an isolated GALR2 receptor protein. This invention further provides DNA, cDNA, genomic DNA, RNA, and mRNA encoding the GALR2 receptor.

This invention further provides a vector comprising the GALR2 receptor. This invention also provides a plasmid which comprises the regulatory elements necessary for expression of GALR2 nucleic acid in a mammalian cell operatively linked to the nucleic acid encoding the GALR2 receptor as to permit expression thereof, designated K985 (ATCC Accession No. 97426). This invention provides mammalian cells comprising the above-described plasmid or vector. This invention also provides a membrane preparation isolated from the cells.

This invention provides a nucleic acid probe comprising a nucleic acid molecule which specifically hybridizes with a nucleic acid encoding a GALR2 receptor, wherein the probe comprises a unique sequence of at least 15 nucleotides within a fragment of (a) the nucleic acid sequence contained in plasmid K985 or (b) the antisense nucleic acid sequence capable of specifically hybridizing to the nucleic acid sequence contained in plasmid K985. In an embodiment, the GALR2 receptor is encoded by the coding sequence of the plasmid K985. This invention further provides a nucleic acid probe comprising a nucleic acid molecule of at least 15 nucleotides which is complementary to a unique fragment of the sequence of a nucleic acid molecule encoding a GALR2 receptor. This invention also provides a nucleic acid probe comprising a nucleic acid molecule of at least 15 nucleotides which is complementary to the antisense sequence of a unique fragment of the sequence of a nucleic acid molecule encoding a GALR2 receptor.

This invention provides an antisense oligonucleotide having a sequence capable of specifically hybridizing to mRNA encoding a GALR2 galanin receptor, so as to prevent translation of the mRNA. This invention also provides an antisense oligonucleotide having a sequence capable of specifically hybridizing to the genomic DNA molecule encoding a GALR2 receptor.

This invention provides an antibody directed to a GALR2 receptor. This invention also provides a monoclonal antibody directed to an epitope of a GALR2 receptor, which epitope is present on the surface of a cell expressing a GALR2 receptor.

This invention provides a pharmaceutical composition comprising an amount of the oligonucleotide effective to reduce activity of a GALR2 receptor by passing through a cell membrane and binding specifically with mRNA encoding a GALR2 receptor in the cell so as to prevent its translation and a pharmaceutically acceptable carrier capable of passing through a cell membrane. In an embodiment, the oligonucleotide is coupled to a substance which inactivates mRNA. In another embodiment, the substance which inactivates mRNA is a ribozyme.

This invention provides a pharmaceutical composition comprising an amount of an antagonist effective to reduce the activity of a GALR2 receptor and a pharmaceutically acceptable carrier.

This invention provides a pharmaceutical composition comprising an amount of an agonist effective to increase activity of a GALR2 receptor and a pharmaceutically acceptable carrier.

This invention provides a transgenic nonhuman mammal expressing DNA encoding a GALR2 receptor. This invention provides a transgenic nonhuman mammal comprising a homologous recombination knockout of the native GALR2 receptor. This invention provides a transgenic nonhuman mammal whose genome comprises antisense DNA complementary to DNA encoding a GALR2 receptor so placed as to be transcribed into antisense MRNA which is complementary to mRNA encoding a GALR2 receptor and which hybridizes to mRNA encoding a GALR2 receptor thereby reducing its translation.

This invention also provides a method for determining whether a compound can specifically bind to a GALR2 receptor which comprises contacting a cell transfected with and expressing DNA encoding the GALR2 receptor with the compound under conditions permitting binding of compounds to such receptor, and detecting the presence of any such compound specifically bound to the GALR2 receptor, so as to thereby determine whether the ligand specifically binds to the GALR2 receptor.

This invention provides a method for determining whether a compound can specifically bind to a GALR2 receptor which comprises preparing a cell extract from cells transfected with and expressing DNA encoding the GALR2 receptor, isolating a membrane fraction from the cell extract, contacting the membrane fraction with the compound under conditions permitting binding of compounds to such receptor, and detecting the presence of the compound specifically bound to the GALR2 receptor, so as to thereby determine whether the compound specifically binds to the GALR2 receptor.

In one embodiment, the GALR2 receptor is a mammalian GALR2 receptor. In another embodiment, the GALR2 receptor is a rat GALR2 receptor. In still another embodiment, the GALR2 receptor has substantially the same amino acid sequence encoded by the plasmid K985.

This invention provides a method for determining whether a compound is a GALR2 receptor agonist which comprises contacting a cell transfected with and expressing DNA encoding the GALR2 receptor with the compound under conditions permitting the activation of the GALR2 receptor, and detecting an increase in GALR2 receptor activity, so as to thereby determine whether the compound is a GALR2 receptor agonist.

This invention provides a method for determining whether a compound is a GALR2 receptor antagonist which comprises contacting a cell transfected with and expressing DNA encoding the GALR2 receptor with the compound in the presence of a known GALR2 receptor agonist, such as galanin, under conditions permitting the activation of the GALR2 receptor, and detecting a decrease in GALR2 receptor activity, so as to thereby determine whether the compound is a GALR2 receptor antagonist.

This invention provides a compound determined by the above-described methods. In one embodiment of the above-described methods, the compound is not previously known.

This invention provides a method of screening a plurality of chemical compounds not known to bind to a GALR2 receptor to identify a compound which specifically binds to the GALR2 receptor, which comprises (a) contacting cells transfected with and expressing DNA encoding the GALR2 receptor with a compound known to bind specifically to the GALR2 receptor; (b) contacting the preparation of step (a) with the plurality of compounds not known to bind specifically to the GALR2 receptor, under conditions permitting binding of compounds known to bind the GALR2 receptor; (c) determining whether the binding of the compound known to bind to the GALR2 receptor is reduced in the presence of the compounds, relative to the binding of the compound in the absence of the plurality of compounds; and if so (d) separately determining the binding to the GALR2 receptor of each compound included in the plurality of compounds, so as to thereby identify the compound which specifically binds to the GALR2 receptor.

This invention provides a method of screening a plurality of chemical compounds not known to activate a GALR2 receptor to identify a compound which activates the GALR2 receptor which comprises (a) contacting cells transfected with and expressing the GALR2 receptor with the plurality of compounds not known to activate the GALR2 receptor, under conditions permitting activation of the GALR2 receptor; (b) determining whether the activity of the GALR2 receptor is increased in the presence of the compounds; and if so (c) separately determining whether the activation of the GALR2 receptor is increased by each compound included in the plurality of compounds, so as to thereby identify the compound which activates the GALR2 receptor.

This invention provides a method of screening a plurality of chemical compounds not known to inhibit the activation of a GALR2 receptor to identify a compound which inhibits the activation of the GALR2 receptor, which comprises (a) preparing a cell extract from cells transfected with and expressing DNA encoding the GALR2 receptor, isolating a membrane fraction from the cell extract, contacting the membrane fraction with the plurality of compounds in the presence of a known GALR2 receptor agonist, under conditions permitting activation of the GALR2 receptor; (b) determining whether the activation of the GALR2 receptor is reduced in the presence of the plurality of compounds, relative to the activation of the GALR2 receptor in the absence of the plurality of compounds; and if so (c) separately determining the inhibition of activation of the GALR2 receptor for each compound included in the plurality of compounds, so as to thereby identify the compound which inhibits the activation of the GALR2 receptor.

This invention provides a method of detecting expression of a GALR2 receptor by detecting the presence of mRNA coding for the GALR2 receptor which comprises obtaining total mRNA from the cell and contacting the mRNA so obtained with the above-described nucleic acid probe under hybridizing conditions, detecting the presence of mRNA hybridized to the probe, and thereby detecting the expression of the GALR2 receptor by the cell.

This invention provides a method of treating an abnormality in a subject, wherein the abnormality is alleviated by the inhibition of a GALR2 receptor which comprises administering to a subject an effective amount of the above-described pharmaceutical composition effective to decrease the activity of the GALR2 receptor in the subject, thereby treating the abnormality in the subject. In an embodiment, the abnormality is obesity. In another embodiment, the abnormality is bulimia.

This invention provides a method of treating an abnormality in a subject wherein the abnormality is alleviated by the activation of a GALR2 receptor which comprises administering to a subject an effective amount of the above-described pharmaceutical composition effective to activate the GALR2 receptor in the subject. In an embodiment, the abnormal condition is anorexia.

This invention provides a method for diagnosing a predisposition to a disorder associated with the activity of a specific human GALR2 receptor allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a human GALR2 receptor and labelled with a detectable marker; (e) detecting labelled bands which have hybridized to DNA encoding a human GALR2 receptor labelled with a detectable marker to create a unique band pattern specific to the DNA of subjects suffering from the disorder; (f) preparing DNA obtained for diagnosis by steps a–e; and (g) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method of modifying feeding behavior of a subject which comprises administering to the subject an amount of a compound which is a galanin receptor agonist or antagonist effective to increase or decrease the consumption of food by the subject so as to thereby modify feeding behavior of the subject. In an embodiment, the compound is a GALR2 receptor antagonist and the amount is effective to decrease the consumption of food by the subject. In another embodiment the compound is administered in combination with food.

In yet another embodiment the compound is a GALR2 receptor agonist and the amount is effective to increase the consumption of food by the subject. In a still further embodiment, the compound is administered in combination with food. In other embodiments the subject is a vertebrate, a mammal, a human or a canine.

BRIEF DESCRIPTION OF THE FIGURES

FIGS. 3A–3C 3A. Diagram of the intron-exon arrangement of the rat GALR2 receptor cDNA contained in plasmid K985. Untranslated regions are indicated by dark hatched segments, and coding region is unmarked except for light gray hatched segments indicating the location of the transmembrane domains of the rat GALR2 receptor. The black segment indicates the location of the intron. 3B. Splice junction sequences of the rat GALR2 receptor. Nucleotide number 1 is located 45 nucleotides upstream of the start codon (Seq. I.D. No. 9). 3C. Intron sequence of rat GALR2 receptor cDNA contained in plasmid K985. Nucleotide number 1 is located 45 nucleotides upstream of the start codon (Seq. I.D. No. 9).

FIG. 4A-1 and 4A-4: Distribution of total [125I]galanin binding in coronal sections through the hypothalamus and amygdala. FIGS. 4A-2 and 4A-5: Binding which remains in these areas following incubation with 60 nM [D-Trp$^2$]galanin$_{(1-29)}$. FIGS. 4A-3 and 4A-6: Binding obtained after incubation with 5 μM porcine galanin, which represents the non-specific binding condition. FIG. 4B: FIGS. 4B-1 to 4B-8: Higher magnification photomicrographs of the [$^{125}$I]galanin binding sites in the hypothalamus and amygdala. FIG. 4B-1: Total binding in the paraventricular hypothalamic nucleus (PVN), virtually all of which is removed by 60 nM [D-Trp$^2$]galanin$_{(1-29)}$,(panel 3B). FIGS. 4B-3 and 4B-4: Binding in the ventromedial hypothalamus (VMH), lateral hypothalamus (LH), and zona incerta (ZI). In these regions, some [$^{125}$I]galanin binding remains after incubation with 60 nM [D-Trp$^2$]galanin$_{(1-29)}$ (FIG. 4B-4). FIGS. 4B-5 and 4B-7: Total binding in the amygdala. After incubation with 60 nM [D-Trp$^2$]galanin$_{(1-29)}$ (panels 5B and 6B), the binding is markedly reduced in the piriform cortex (Pir), and to a lesser extent in the medial nucleus (Me), and central nucleus (Ce). However, the binding in the nucleus of the lateral olfactory tract (LOT) is largely unaffected. FIG. 4C: Panels 4C-1 to 4C-6: Distribution of [125I]galanin binding sites in the anterior forebrain (panel 7) and in the midbrain (panel 8). In the lateral septum (LS) and insular cortex (CTX), much of the total binding (panel 7A) is removed by 60 nM [D-Trp$^2$]galanin$_{(1-29)}$ (panel 7B) . Similarly, the total binding observed in the superior colliculus (SC), central gray (CG), and pontine reticular nucleus (PnO) (panel 8A) is markedly diminished (panel 8B). FIGS. 4C-3 and 4C-6: Nonspecific binding observed in adjacent sections through the septum and midbrain. Arc, arcuate nucleus; Ce, central amygdaloid nucleus; CL, centrolateral thalamic nucleus; LOT, nucleus of the lateral olfactory tract; Me, medial amygdaloid nucleus; Pir, piriform cortex; PVN, paraventricular hypothalamic nucleus; SO, supraoptic nucleus; st, stria terminalis; VMH, ventromedial hypothalamic nucleus; ZI, zona incerta.

FIG. 5. Reverse transcriptase PCR (RT-PCR) of rat GALR2 receptor mRNA from various brain regions. The blot was hybridized at high stringency with an oligonucleotide probe corresponding to a portion of the predicted V/VI loop of GALR2. Positive controls are indicated by +'s and represent plasmids containing the indicated inserts. Size standards are indicated at the left in kilobases. Note the additional hybridizing bands intermediate in size between the intron-containing and the intronless product.

DETAILED DESCRIPTION OF THE INVENTION

Throughout this application, the following standard abbreviations are used to indicate specific nucleotide bases:

C=cytosine A=adenine

T=thymine G=guanine

Furthermore, the term "agonist" is used throughout this application to indicate any peptide or non-peptidyl compound which increases the activity of any of the receptors of the subject invention. The term "antagonist" is used throughout this application to indicate any peptide or non-peptidyl compound which decreases the activity of any of the receptors of the subject invention.

The activity of a G-protein coupled receptor such as a galanin receptor may be measured using any of a variety of functional assays in which activation of the receptor in question results in an observable change in the level of some second messenger system, including but not limited to adenylate cyclase, calcium mobilization, ion channel activity, inositol phospholipid hydrolysis or guanylyl cyclase. Heterologous expression systems utilizing appropriate host cells to express the nucleic acid of the subject invention are used to obtain the desired second messenger coupling. Receptor activity may also be assayed in an oocyte expression system.

This invention provides an isolated nucleic acid encoding a GALR2 galanin receptor. In an embodiment, the galanin receptor is a vertebrate or a mammalian GALR2 receptor. In another embodiment, the galanin receptor is a rat GALR2 receptor. In another embodiment, the galanin receptor is a human GALR2 receptor. In an embodiment, the isolated nucleic acid encodes a receptor characterized by an amino acid sequence in the transmembrane region, which has a homology of 60% or higher to the amino acid sequence in the transmembrane region of the rat galanin GALR2 receptor and a homology of less than 60% to the amino acid sequence in the transmembrane region of any GALR1 receptor. In an embodiment, the GALR2 receptor is a rat GALR2 receptor. In another embodiment, the GALR2 receptor is a human GALR2 receptor.

Figure 3A:
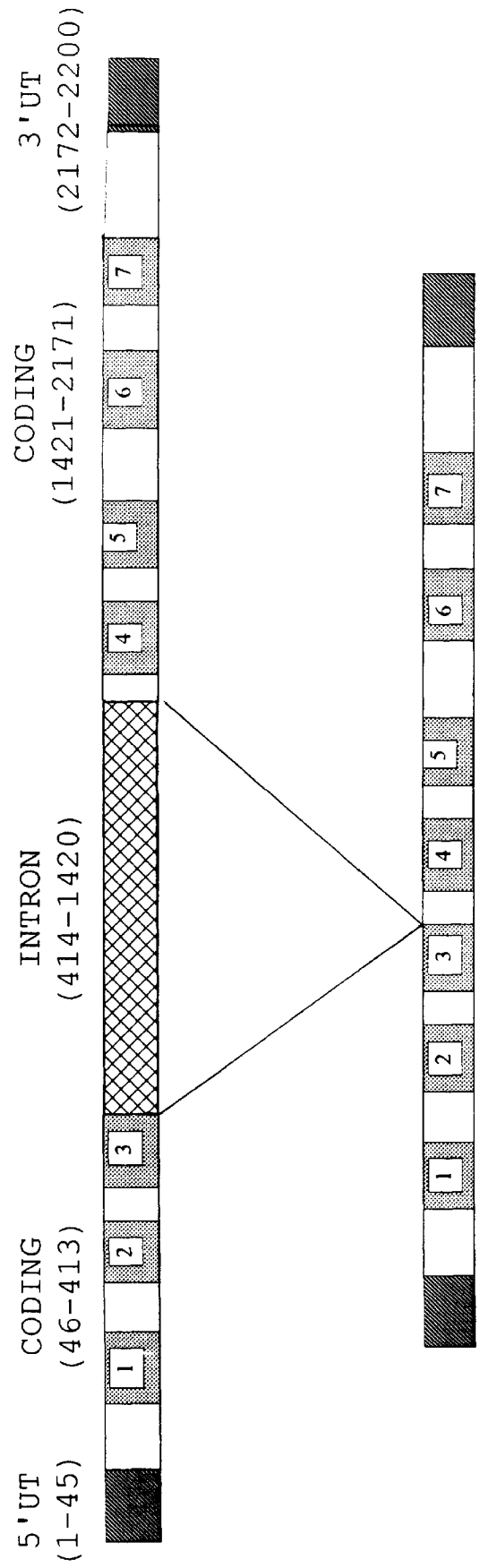
Figures 1, 4A:
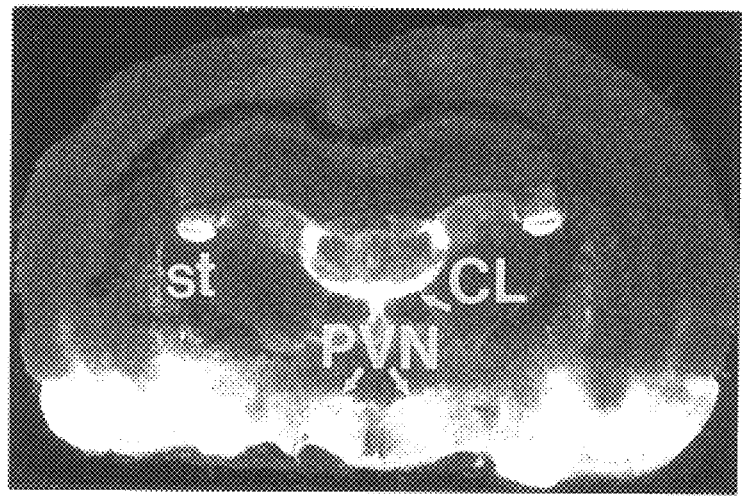
FIG. 1 Nucleotide coding sequence of the rat hypothalamic galanin GALR2 receptor (Seq. I.D. No. 7), with partial 5' and 3' untranslated sequences. Start (ATG) and stop (TAA) codons are underlined.
FIGS. 4A–4C Localization of [$^{125}$I]galanin binding sites in rat CNS.
Figures 2, 4A:
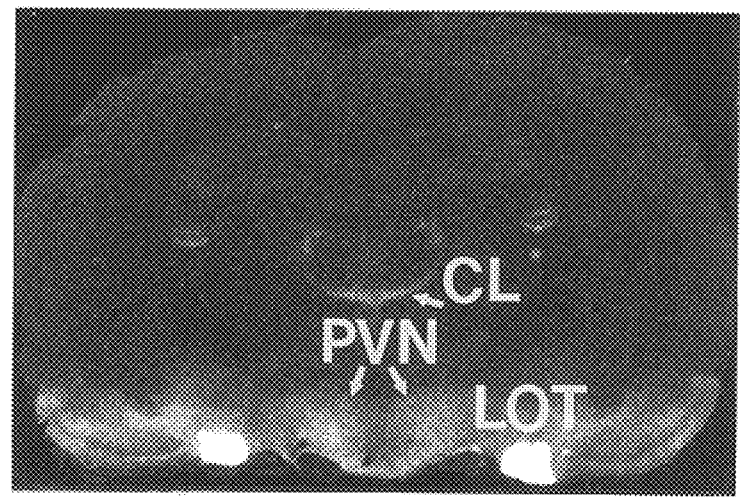
FIG. 2 Deduced amino acid sequence of the rat hypothalamic galanin GALR2 receptor encoded by the nucleotide sequence shown in FIG. 1 (Seq. I.D. No. 8).

This invention provides an isolated nucleic acid encoding a GALR2 receptor having substantially the same amino acid sequence as shown in FIG. 2. In an embodiment, the nucleic acid is DNA. This invention further provides an isolated nucleic acid encoding a rat GALR2 receptor having the amino acid sequence shown in FIG. 2. In another embodiment, the nucleic acid comprises at least an intron. In yet another embodiment, the intron comprises a fragment of the intron sequence shown in FIG. 3C (Seq. I.D. No. 9). In still another embodiment, the nucleic acid comprises alternately spliced nucleic acid transcribed from the nucleic acid contained in plasmid K985. In an embodiment, the alternately spliced nucleic acid is mRNA transcribed from DNA encoding a galanin receptor.

In an embodiment, the GALR2 receptor has substantially the same amino acid sequence as the amino acid sequence encoded by plasmid K985 (ATCC Accession No. 97426). In yet another embodiment, the GALR2 receptor has the amino acid sequence encoded by the plasmid K985.

This invention provides the above-described isolated nucleic acid, wherein the nucleic acid is DNA. In an embodiment, the DNA is cDNA. In another embodiment, the DNA is genomic DNA. In still another embodiment, the nucleic acid molecule is RNA. Methods for production and manipulation of nucleic acid molecules are well known in the art.

In another embodiment, the nucleic acid encodes a vertebrate GALR2 receptor. In a separate embodiment, the nucleic acid encodes a mammalian GALR2 receptor. In another embodiment, the nucleic acid encodes a rat GALR2 receptor. In still another embodiment, the nucleic acid encodes a human GALR2 receptor.

This invention further provides nucleic acid which is degenerate with the DNA comprising the coding sequence of the plasmid K985. This invention further provides nucleic acid which is degenerate with any DNA encoding a GALR2 receptor. In an embodiment, the nucleic acid comprises a nucleotide sequence which is degenerate with the nucleotide sequence described in FIG. 1 (Seq. I.D. No. 1), that is, a nucleotide sequence which is translated into the same amino acid sequence. In another embodiment, the nucleic acid comprises a nucleotide sequence which is degenerate with the nucleotide sequence described in Seq. I.D. No. 9.

This invention also encompasses DNAs and cDNAs which encode amino acid sequences which differ from those of the GALR2 galanin receptor, but which should not produce phenotypic changes. Alternatively, this invention also encompasses DNAs, cDNAs, and RNAs which hybridize to the DNA, cDNA, and RNA of the subject invention. Hybridization methods are well known to those of skill in the art.

The nucleic acids of the subject invention also include nucleic acid molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The nucleic acids described and claimed herein are useful for the information which they provide concerning the amino acid sequence of the polypeptide and as products for the large scale synthesis of the polypeptide by a variety of recombinant techniques. The nucleic acid molecule is useful for generating new cloning and expression vectors, transformed and transfected prokaryotic and eukaryotic host cells, and new and useful methods for cultured growth of such host cells capable of expression of the polypeptide and related products.

This invention also provides an isolated galanin GALR2 receptor protein. In an embodiment, the GALR2 receptor protein has substantially the same amino acid sequence as shown in FIG. 2. In another embodiment, the GALR2 receptor has the amino acid sequence shown in FIG. 2.

This invention provides a vector comprising the above-described nucleic acid molecule.

Vectors which comprise the isolated nucleic acid molecule described hereinabove also are provided. Suitable vectors comprise, but are not limited to, a plasmid or a virus. These vectors may be transformed into a suitable host cell to form a host cell expression system for the production of a polypeptide having the biological activity of a galanin GALR2 receptor. Suitable host cells include, for example, neuronal cells such as the glial cell line C6, a Xenopus cell such as an oocyte or melanophore cell, as well as numerous mammalian cells and non-neuronal cells.

This invention provides the above-described vector adapted for expression in a bacterial cell which further comprises the regulatory elements necessary for expression of the nucleic acid in the bacterial cell operatively linked to the nucleic acid encoding the GALR2 receptor as to permit expression thereof.

This invention provides the above-described vector adapted for expression in a yeast cell which comprises the regulatory elements necessary for expression of the nucleic acid in the yeast cell operatively linked to the nucleic acid encoding the GALR2 receptor as to permit expression thereof.

This invention provides the above-described vector adapted for expression in an insect cell which comprises the regulatory elements necessary for expression of the nucleic acid in the insect cell operatively linked to the nucleic acid encoding the GALR2 receptor as to permit expression thereof. In a still further embodiment, the vector is a baculovirus.

In an embodiment, the vector is adapted for expression in a mammalian cell which comprises the regulatory elements necessary for expression of the nucleic acid in the mammalian cell operatively linked to the nucleic acid encoding the mammalian GALR2 receptor as to permit expression thereof.

In a further embodiment, the vector is adapted for expression in a mammalian cell which comprises the regulatory elements necessary for expression of the nucleic acid in the mammalian cell operatively linked to the nucleic acid encoding the rat GALR2 receptor as to permit expression thereof.

In a still further embodiment, the vector is a plasmid.

In another embodiment, the plasmid is adapted for expression in a mammalian cell which comprises the regulatory elements necessary for expression of the nucleic acid in the mammalian cell operatively linked to the nucleic acid encoding the human GALR2 receptor as to permit expression thereof.

This invention provides the above-described plasmid adapted for expression in a mammalian cell which comprises the regulatory elements necessary for expression of nucleic acid in a mammalian cell operatively linked to the nucleic acid encoding the mammalian GALR2 receptor as to permit expression thereof.

This invention provides a plasmid which comprises the regulatory elements necessary for expression of DNA in a mammalian cell operatively linked to the DNA encoding the GALR2 galanin receptor as to permit expression thereof designated K985 (ATCC Accession No. 97426).

This plasmid (K985) was deposited on Jan. 24, 1996, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. 97426.

This invention provides a eukaryotic cell comprising the above-described plasmid or vector. This invention provides a mammalian cell comprising the above-described plasmid or vector. In an embodiment the cell is a *Xenopus oocyte* or melanophore cell. In an embodiment, the cell is a neuronal cell such as the glial cell line C6. In an embodiment, the mammalian cell is non-neuronal in origin. In an embodiment, the mammalian cell is a COS-7 cell. In another embodiment the mammalian cell is a Chinese hamster ovary (CHO) cell.

In still another embodiment, the mammalian cell is a 293 human embryonic kidney cell. In still another embodiment, the mammalian cell is a NIH-3T3 cell. In another embodiment, the mammalian cell is an LM(tk-) cell. In still another embodiment, the mammalian cell is the LM(tk-) cell designated L-rGALR2-8. This cell line was deposited with the ATCC on Mar. 28, 1996, under the provisions of the Budapest Treaty for the International Recognition of the Deposit of Microorganisms for the Purposes of Patent Procedure, and was accorded ATCC Accession No. CRL-12074.

This invention also provides an insect cell comprising the above-described vector. In an embodiment, the insect cell is an Sf9 cell. In another embodiment, the insect cell is an Sf21 cell.

This invention provides a membrane preparation isolated from any of the above-described cells.

Figures 3, 4A:
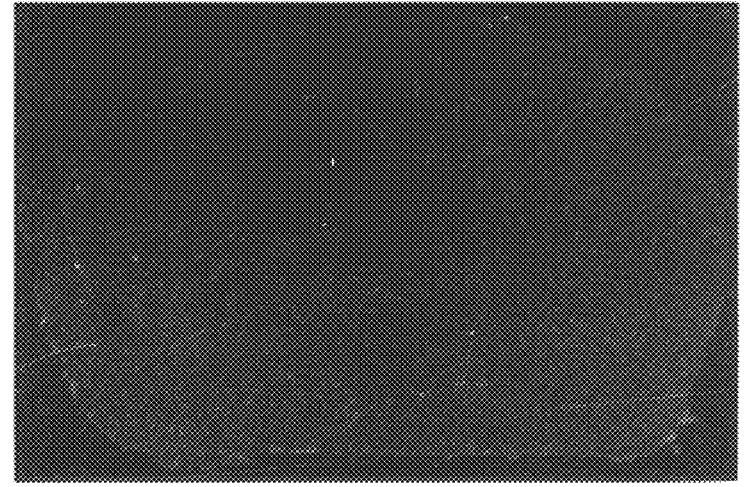
Figures 4, 4A:
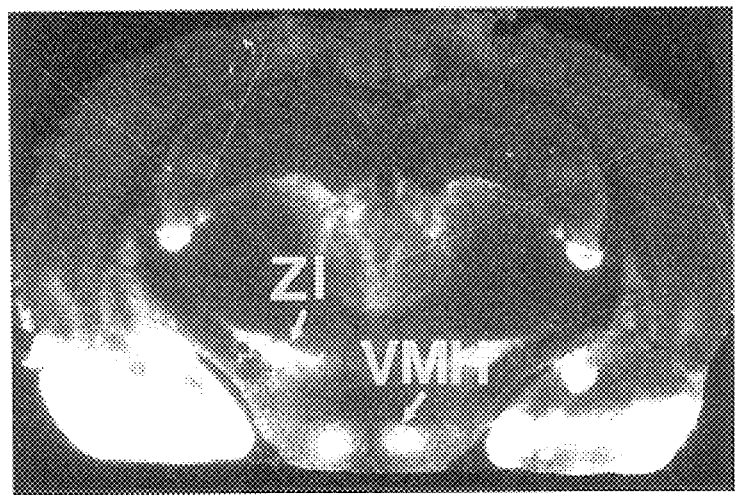

This invention provides a nucleic acid probe comprising a nucleic acid which specifically hybridizes with a nucleic acid encoding a GALR2 receptor, wherein the probe comprises a unique sequence of at least 15 nucleotides within a fragment of (a) the nucleic acid sequence contained in plasmid K985 or (b) the antisense nucleic acid sequence capable of specifically hybridizing to the nucleic acid sequence contained in plasmid K985. In one embodiment the GALR2 receptor is encoded by the coding sequence of the plasmid K985, or the reverse complement (antisense sequence) of the coding sequence of plasmid K985. This invention provides a nucleic acid probe comprising a nucleic acid which specifically hybridizes with a nucleic acid encoding a GALR2 receptor, wherein the probe comprises a unique sequence of at least 15 nucleotides within a fragment of (a) the nucleic acid sequence described in FIG. 1 (Seq. I.D. No. 7) or (b) the antisense nucleic acid sequence capable of specifically hybridizing to the nucleic acid sequence described in FIG. 1 (Seq. I.D. No. 7). In an embodiment, the nucleic acid encoding a GALR2 receptor comprises an intron, the sequence of which intron is described in FIG. 3 (Seq. I.D. No. 9). This invention further provides a nucleic acid probe comprising a nucleic acid molecule of at least 15 nucleotides which is complementary to a unique fragment of the sequence of a nucleic acid molecule encoding a GALR2 receptor. This invention also provides a nucleic acid probe comprising a nucleic acid molecule of at least 15 nucleotides which is complementary to the antisense sequence of a unique fragment of the sequence of a nucleic acid molecule encoding a GALR2 receptor.

In an embodiment, the nucleic acid probe is DNA. In another embodiment the nucleic acid probe is RNA. As used herein, the phrase "specifically hybridizing" means the ability of a nucleic acid molecule to recognize a nucleic acid sequence complementary to its own and to form double-helical segments through hydrogen bonding between complementary base pairs.

This nucleic acid of at least 15 nucleotides capable of specifically hybridizing with a sequence of a nucleic acid encoding the GALR2 galanin receptors can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes the GALR2 receptor into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the DNA molecule which encodes the GALR2 galanin receptor downstream of a bacteriophage promoter such as T3, T7 or SP6. Large amounts of RNA probe may be produced by incubating the labeled nucleotides with the linearized fragment where it contains an upstream promoter in the presence of the appropriate RNA polymerase.

This invention provides an antisense oligonucleotide having a sequence capable of specifically hybridizing to mRNA encoding a GALR2 galanin receptor, so as to prevent translation of the mRNA.

This invention provides an antisense oligonucleotide having a sequence capable of specifically hybridizing to the genomic DNA molecule encoding a GALR2 receptor.

This invention provides an antisense oligonucleotide comprising chemical analogues of nucleotides.

This invention provides an antibody directed to a GALR2 receptor. This invention also provides an antibody directed to a rat GALR2 receptor. This invention also provides an antibody directed to a human GALR2 receptor.

This invention provides a monoclonal antibody directed to an epitope of a GALR2 receptor, which epitope is present on the surface of a cell expressing a GALR2 receptor.

This invention provides a pharmaceutical composition comprising an amount of the oligonucleotide effective to reduce activity of a GALR2 receptor by passing through a cell membrane and binding specifically with mRNA encoding a GALR2 receptor in the cell so as to prevent its translation and a pharmaceutically acceptable carrier capable of passing through a cell membrane. In an embodiment, the oligonucleotide is coupled to a substance which inactivates mRNA. In another embodiment, the substance which inactivates mRNA is a ribozyme.

This invention provides the above-described pharmaceutical composition, wherein the pharmaceutically acceptable carrier capable of passing through a cell membrane comprises a structure which binds to a receptor specific for a selected cell type and is thereby taken up by cells of the selected cell type.

This invention provides a pharmaceutical composition comprising an amount of an antagonist effective to reduce the activity of a GALR2 receptor and a pharmaceutically acceptable carrier.

This invention provides a pharmaceutical composition comprising an amount of an agonist effective to increase activity of a GALR2 receptor and a pharmaceutically acceptable carrier.

This invention provides the above-described pharmaceutical composition which comprises an amount of the antibody effective to block binding of a ligand to the GALR2 receptor and a pharmaceutically acceptable carrier.

As used herein, "pharmaceutically acceptable carriers" means any of the standard pharmaceutically acceptable carriers. Examples include, but are not limited to, phosphate buffered saline, physiological saline, water and emulsions, such as oil/water emulsions.

This invention provides a transgenic nonhuman mammal expressing DNA encoding a GALR2 receptor.

This invention provides a transgenic nonhuman mammal comprising a homologous recombination knockout of the native GALR2 receptor.

This invention provides a transgenic nonhuman mammal whose genome comprises antisense DNA complementary to DNA encoding a GALR2 receptor so placed as to be transcribed into antisense mRNA which is complementary to mRNA encoding a GALR2 receptor and which hybridizes to mRNA encoding a GALR2 receptor thereby reducing its translation.

This invention provides the above-described transgenic nonhuman mammal, wherein the DNA encoding a GALR2 receptor additionally comprises an inducible promoter.

This invention provides the transgenic nonhuman mammal, wherein the DNA encoding a GALR2 receptor additionally comprises tissue specific regulatory elements.

In an embodiment, the transgenic nonhuman mammal is a mouse.

Animal model systems which elucidate the physiological and behavioral roles of GALR2 receptor are produced by creating transgenic animals in which the activity of the GALR2 receptor is either increased or decreased, or the amino acid sequence of the expressed GALR2 receptor is altered, by a variety of techniques. Examples of these techniques include, but are not limited to: 1) Insertion of normal or mutant versions of DNA encoding a GALR2 receptor, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus in transgenic animals to alter the regulation of expression or the structure of these GALR2 receptor sequences. The technique of homologous recombination is well known in the art. It replaces the native gene with the inserted gene and so is useful for producing an animal that cannot express native GALR2 receptors but does express, for example, an inserted mutant GALR2 receptor, which has replaced the native GALR2 receptor in the animal's genome by recombination, resulting in underexpression of the transporter. Microinjection adds genes to the genome, but does not remove them, and so is useful for producing an animal which expresses its own and added GALR2 receptors, resulting in overexpression of the GALR2 receptors.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a GALR2 receptor is purified from a vector by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term.

As noted above, microinjection is not the only method for inserting DNA into the egg cell, and is used here only for exemplary purposes.

This invention also provides a method for determining whether a chemical compound can specifically bind to a GALR2 receptor which comprises contacting a cell transfected with and expressing DNA encoding the GALR2 receptor with the compound under conditions permitting binding of compounds to such receptor, and detecting the presence of any such compound specifically bound to the GALR2 receptor, so as to thereby determine whether the ligand specifically binds to the GALR2 receptor.

This invention provides a method for determining whether a chemical compound can specifically bind to a GALR2 receptor which comprises preparing a cell extract from cells transfected with and expressing DNA encoding the GALR2 receptor, isolating a membrane fraction from the cell extract, contacting the membrane fraction with the compound under conditions permitting binding of compounds to such receptor, and detecting the presence of the compound specifically bound to the GALR2 receptor, so as to thereby determine whether the compound specifically binds to the GALR2 receptor.

In one embodiment, the GALR2 receptor is a mammalian GALR2 receptor. In another embodiment, the GALR2 receptor is a rat GALR2 receptor. In still another embodiment, the GALR2 receptor has substantially the same amino acid sequence as that encoded by the plasmid K985. In still another embodiment, the GALR2 receptor has substantially the same amino acid sequence as the amino acid sequence shown in FIG. 2 (Seq. I.D. No. 8). In yet another embodiment, the GALR2 receptor has the amino acid sequence shown in FIG. 2 (Seq. I.D. No. 8).

This invention provides a method for determining whether a chemical compound is a GALR2 receptor agonist which comprises contacting a cell transfected with and expressing DNA encoding the GALR2 receptor with the compound under conditions permitting the activation of the GALR2 receptor, and detecting an increase in GALR2 receptor activity, so as to thereby determine whether the compound is a GALR2 receptor agonist.

This invention provides a method for determining whether a chemical compound is a GALR2 receptor agonist which comprises preparing a cell extract from cells transfected with and expressing DNA encoding the GALR2 receptor, isolating a membrane fraction from the cell extract, contacting the membrane fraction with the compound under conditions permitting the activation of the GALR2 receptor, and detecting an increase in GALR2 receptor activity, so as to thereby determine whether the compound is a GALR2 receptor agonist.

In an embodiment, the GALR2 receptor is a rat GALR2 receptor. In another embodiment, the GALR2 receptor has substantially the same amino acid sequence as that encoded by the plasmid K985. In still another embodiment, the GALR2 receptor has substantially the same amino acid sequence as the amino acid sequence shown in FIG. 2 (Seq. I.D. No.8). In yet another embodiment, the GALR2 receptor has the amino acid sequence shown in FIG. 2 (Seq. I.D. No. 8).

This invention provides a method for determining whether a chemical compound is a GALR2 receptor antagonist which comprises contacting a cell transfected with and expressing DNA encoding the GALR2 receptor with the compound in the presence of a known GALR2 receptor agonist, such as galanin, under conditions permitting the activation of the GALR2 receptor, and detecting a decrease in GALR2 receptor activity, so as to thereby determine whether the compound is a GALR2 receptor antagonist.

This invention provides a method for determining whether a chemical compound is a GALR2 receptor antagonist which comprises preparing a cell extract from cells transfected with and expressing DNA encoding the GALR2 receptor, isolating a membrane fraction from the cell extract, contacting the membrane fraction with the ligand in the presence of a known GALR2 receptor agonist, such as galanin, under conditions permitting the activation of the GALR2 receptor, and detecting a decrease in GALR2 receptor activity, so as to thereby determine whether the compound is a GALR2 receptor antagonist.

In an embodiment of the invention, the GALR2 receptor is a rat GALR2 receptor. In another embodiment, the GALR2 receptor has substantially the same amino acid sequence as that encoded by the plasmid K985. In still another embodiment, the GALR2 receptor has substantially the same amino acid sequence as the amino acid sequence shown in FIG. 2 (Seq. I.D. No. 8). In yet another embodiment, the GALR2 receptor has the amino acid sequence shown in FIG. 2 (Seq. I.D. No. 8).

In an embodiment of the above-described methods, the cell is an insect cell. In another embodiment, the cell is a mammalian cell. In a further embodiment, the cell is non-neuronal in origin. In still further embodiments, the non-neuronal cell is a COS-7 cell, 293 human embryonic kidney cell, NIH-3T3 cell, a CHO cell, or LM(tk-) cell.

This invention provides a compound determined by the above-described methods. In one embodiment of the above-described methods, the compound is not previously known.

This invention provides a GALR2 agonist determined by the above-described methods. This invention also provides a GALR2 antagonist determined by the above-described methods.

This invention provides a pharmaceutical composition which comprises an amount of a GALR2 receptor agonist effective to increase activity of a GALR2 receptor and a pharmaceutically acceptable carrier.

This invention provides a pharmaceutical composition which comprises an amount of a GALR2 receptor antagonist effective to reduce activity of a GALR2 receptor and a pharmaceutically acceptable carrier.

In further embodiments of the above-described methods, the agonist or antagonist is not previously known.

This invention provides a method of screening a plurality of chemical compounds not known to bind to a GALR2 receptor to identify a compound which specifically binds to the GALR2 receptor, which comprises (a) contacting cells transfected with and expressing DNA encoding the GALR2 receptor with a compound known to bind specifically to the GALR2 receptor; (b) contacting the preparation of step (a) with the plurality of compounds not known to bind specifically to the GALR2 receptor, under conditions permitting binding of compounds known to bind the GALR2 receptor; (c) determining whether the binding of the compound known to bind to the GALR2 receptor is reduced in the presence of the compounds, relative to the binding of the compound in the absence of the plurality of compounds; and if so (d) separately determining the binding to the GALR2 receptor of each compound included in the plurality of compounds, so as to thereby identify the compound which specifically binds to the GALR2 receptor.

This invention provides a method of screening a plurality of chemical compounds not known to bind to a GALR2 receptor to identify a compound which specifically binds to the GALR2 receptor, which comprises (a) preparing a cell extract from cells transfected with and expressing DNA encoding the GALR2 receptor, isolating a membrane fraction from the cell extract, contacting the membrane fraction with a compound known to bind specifically to the GALR2 receptor; (b) contacting the preparation of step (a) with the plurality of compounds not known to bind specifically to the GALR2 receptor, under conditions permitting binding of compounds known to bind the GALR2 receptor; (c) determining whether the binding of the compound known to bind to the GALR2 receptor is reduced in the presence of the compounds, relative to the binding of the compound in the absence of the plurality of compounds; and if so (d) separately determining the binding to the GALR2 receptor of each compound included in the plurality of compounds, so as to thereby identify the compound which specifically binds to the GALR2 receptor.

In an embodiment of the above-described methods, the GALR2 receptor is a rat GALR2 receptor. In another embodiment, the GALR2 receptor has substantially the same amino acid sequence as the amino acid sequence shown in FIG. 2 (Seq. I.D. No.8). In yet another embodiment, the GALR2 receptor has the amino acid sequence shown in FIG. 2 (Seq. I.D. No. 8).

This invention provides a method of screening a plurality of chemical compounds not known to activate a GALR2 receptor to identify a compound which activates the GALR2 receptor which comprises (a) contacting cells transfected with and expressing the GALR2 receptor with the plurality of compounds not known to activate the GALR2 receptor, under conditions permitting activation of the GALR2 receptor; (b) determining whether the activity of the GALR2 receptor is increased in the presence of the compounds; and if so (c) separately determining whether the activation of the GALR2 receptor is increased by each compound included in the plurality of compounds, so as to thereby identify the compound which activates the GALR2 receptor.

This invention provides a method of screening a plurality of chemical compounds not known to activate a GALR2 receptor to identify a compound which activates the GALR2 receptor which comprises (a) preparing a cell extract from cells transfected with and expressing DNA encoding the GALR2 receptor, isolating a membrane fraction from the cell extract, contacting the membrane fraction with the plurality of compounds not known to activate the GALR2 receptor, under conditions permitting activation of the GALR2 receptor; (b) determining whether the activity of the GALR2 receptor is increased in the presence of the compounds; and if so (c) separately determining whether the activation of the GALR2 receptor is increased by each compound included in the plurality of compounds, so as to thereby identify the compound which activates the GALR2 receptor.

In an embodiment of the above-described methods, the GALR2 receptor is a rat GALR2 receptor. In still another embodiment, the GALR2 receptor has substantially the same amino acid sequence as the amino acid sequence shown in FIG. 2 (Seq. I.D. No. 8). In yet another embodiment, the GALR2 receptor has the amino acid sequence shown in FIG. 2 (Seq. I.D. No. 8).

This invention provides a method of screening a plurality of chemical compounds not known to inhibit the activation of a GALR2 receptor to identify a compound which inhibits the activation of the GALR2 receptor, which comprises (a) contacting cells transfected with and expressing the GALR2 receptor with the plurality of compounds in the presence of a known GALR2 receptor agonist, under conditions permitting activation of the GALR2 receptor; (b) determining whether the activation of the GALR2 receptor is reduced in the presence of the plurality of compounds, relative to the activation of the GALR2 receptor in the absence of the plurality of compounds; and if so (c) separately determining the inhibition of activation of the GALR2 receptor for each compound included in the plurality of compounds, so as to thereby identify the compound which inhibits the activation of the GALR2 receptor.

This invention provides a method of screening a plurality of chemical compounds not known to inhibit the activation of a GALR2 receptor to identify a compound which inhibits the activation of the GALR2 receptor, which comprises (a) preparing a cell extract from cells transfected with and expressing DNA encoding the GALR2 receptor, isolating a membrane fraction from the cell extract, contacting the membrane fraction with the plurality of compounds in the presence of a known GALR2 receptor agonist, under conditions permitting activation of the GALR2 receptor; (b) determining whether the activation of the GALR2 receptor is reduced in the presence of the plurality of compounds, relative to the activation of the GALR2 receptor in the absence of the plurality of compounds; and if so (c) separately determining the inhibition of activation of the GALR2 receptor for each compound included in the plurality of compounds, so as to thereby identify the compound which inhibits the activation of the GALR2 receptor.

In an embodiment of the above-described methods, the GALR2 receptor is a rat GALR2 receptor. In another embodiment, the GALR2 receptor has substantially the same amino acid sequence as the amino acid sequence shown in FIG. 2 (Seq. I.D. No. 8). In yet another embodiment, the GALR2 receptor has the amino acid sequence shown in FIG. 2 (Seq. I.D. No. 8).

In an embodiment of any of the above-described methods, the activation of the GALR2 receptor is determined by a second messenger assay. In an embodiment, the second messenger assay measures adenylate cyclase activity. In another embodiment, the second messenger is cyclic AMP or a phosphoinositol lipid metabolite.

This invention further provides a method of measuring GALR2 receptor activation in an oocyte expression system such as a *Xenopus oocyte* or melanophore. In an embodiment, receptor activation is determined by measurement of ion channel activity.

Expression of genes in *Xenopus oocytes* is well known in the art (A. Coleman, *Transcription and Translation: A Practical Approach* (B. D. Hanes, S. J. Higgins, eds., pp 271–302, IRL Press, Oxford, 1984; Y. Masu et al., *Nature* 329:21583–21586, 1994) and is performed using microinjection of native mRNA or in vitro synthesized mRNA into frog oocytes. The preparation of in vitro synthesized mRNA can be performed by various standard techniques (J. Sambrook et al., *Molecular Cloning: A Laboratory Manual*, Second Edition, Cold Spring Harbor Laboratory, Cold Spring Harbor, New York, 1989) including using T7 polymerase with the mCAP RNA capping kit (Stratagene).

In a further embodiment of the invention, the cell is a mammalian cell. In another embodiment of the invention, the mammalian cell is non-neuronal in origin. In still further embodiments of the invention, the non-neuronal cell is a COS-7 cell, a 293 human embryonic kidney cell, a LM(tk-) cell, a CHO cell, or an NIH-3T3 cell. In an embodiment of the invention, the nonneuronal cell is the LM(tk-) cell designated L-rGALR2-8 (ATCC Accession No. CRL-12074).

This invention provides a pharmaceutical composition comprising a compound identified by the above-described methods and a pharmaceutically acceptable carrier.

In an embodiment of the above-described methods, the cell is non-neuronal in origin. In a further embodiment, the non-neuronal cell is a COS-7 cell, 293 human embryonic kidney cell, NIH-3T3 cell or LM(tk-) cell.

In one embodiment of the above-described methods, the compound is not previously known.

This invention provides a GALR2 receptor agonist detected by the above-described methods. This invention provides a GALR2 receptor antagonist detected by the above-described methods. In an embodiment the cell is a non-mammalian cell, for example, a *Xenopus oocyte* or melanophore. In another embodiment the cell is a neuronal cell, for example, a glial cell line such as C6.

In an embodiment, the cell is non-neuronal in origin. In a further embodiment, the cell is a Cos-7 or a CHO cell, a 293 human embryonic kidney cell, an LM(tk-) cell or an NIH-3T3 cell. In an embodiment of the invention, the LM(tk-) cell is the cell designated L-rGALR2-8 (ATCC Accession No. CRL-12074).

This invention provides a pharmaceutical composition comprising a drug candidate identified by the above-described methods and a pharmaceutically acceptable carrier.

This invention provides a method for determining whether a chemical compound is a GALR2 antagonist which comprises: (a) administering to an animal a GALR2 agonist and measuring the amount of food intake in the animal; (b) administering to a second animal both the GALR2 agonist and the chemical compound, and measuring the amount of food intake in the second animal; and (c) determining whether the amount of food intake is reduced in the presence of the chemical compound relative to the amount of food intake in the absence of the compound, so as to thereby determine whether the compound is a GALR2 antagonist. This invention further provides a method of screening a plurality of chemical compounds to identify a chemical compound which is a GALR2 antagonist which comprises: (a) administering to an animal a GALR2 agonist and measuring the amount of food intake in the animal; (b) administering to a second animal the GALR2 agonist and at least one chemical compound of the plurality of compounds, and measuring the amount of food intake in the animal; (c) determining whether the amount of food intake is reduced in the presence of at least one chemical compound compound of the plurality of chemcial compounds relative to the amount of food intake in the absence of at least one of the compounds, and if so; (d) separately determining whether each chemical compound is a GALR2 antagonist according to the method described above, so as to thereby determine if the chemical compound is a GALR2 antagonist. In one embodiment the GALR2 agonist is $[D-Trp]_2$-galanin$_{(1-29)}$.

In another embodiment the animal is a non-human mammal. In a further embodiment, the animal is a rodent.

This invention provides a method of detecting expression of a GALR2 receptor by detecting the presence of mRNA coding for the GALR2 receptor which comprises obtaining total mRNA from a cell or tissue sample and contacting the mRNA so obtained with the above-described nucleic acid probe under hybridizing conditions, detecting the presence of mRNA hybridized to the probe, and thereby detecting the expression of the GALR2 receptor by the cell or in the tissue.

This invention provides a method of treating an abnormality in a subject, wherein the abnormality is alleviated by administering to the subject an amount of a GALR2 selective compound, effective to treat the abnormality. Abnormalities which may be treated include cognitive disorder, pain, sensory disorder (olfactory, visual), motor coordination abnormality, motion sickness, neuroendocrine disorders, sleep disorders, migraine, Parkinson's disease, hypertension, heart failure, convulsion/epilepsy, traumatic brain injury, diabetes, glaucoma, electrolyte imbalances, respiratory disorders (asthma, emphysema), depression, reproductive disorders, gastric and intestinal ulcers, gastroesophageal reflux disorder, gastric hypersecretion, gastrointestinal motility disorders (diarrhea), inflammation, immune disorders, and anxiety. In one embodiment the compound is an agonist. In another embodiment the compound is an antagonist.

This invention provides a method of treating an abnormality in a subject, wherein the abnormality is alleviated by the inhibition of a GALR2 receptor which comprises administering to a subject an effective amount of the above-described pharmaceutical composition effective to decrease the activity of the GALR2 receptor in the subject, thereby treating the abnormality in the subject. In an embodiment, the abnormality is obesity. In another embodiment, the abnormality is bulimia.

This invention provides a method of treating an abnormality in a subject wherein the abnormality is alleviated by the activation of a GALR2 receptor which comprises administering to a subject an effective amount of the above-described pharmaceutical composition effective to activate the GALR2 receptor in the subject. In an embodiment, the abnormal condition is anorexia.

This invention provides a method of detecting the presence of a GALR2 receptor on the surface of a cell which comprises contacting the cell with the above-described antibody under conditions permitting binding of the antibody to the receptor, detecting the presence of the antibody bound to the cell, and thereby detecting the presence of a GALR2 receptor on the surface of the cell.

This invention provides a method of determining the physiological effects of varying levels of activity of GALR2 receptors which comprises producing a transgenic nonhuman mammal whose levels of GALR2 receptor activity are varied by use of an inducible promoter which regulates GALR2 receptor expression.

This invention provides a method of determining the physiological effects of varying levels of activity of GALR2 receptors which comprises producing a panel of transgenic nonhuman mammals each expressing a different amount of GALR2 receptor.

This invention provides a method for identifying an antagonist capable of alleviating an abnormality wherein the abnormality is alleviated by decreasing the activity of a GALR2 receptor comprising administering a compound to the above-described transgenic nonhuman mammal and determining whether the compound alleviates the physical and behavioral abnormalities displayed by the transgenic nonhuman mammal as a result of overactivity of a GALR2 receptor, the alleviation of the abnormality identifying the compound as an antagonist.

This invention provides an antagonist identified by the above-described methods. This invention provides a pharmaceutical composition comprising an antagonist identified by the above-described methods and a pharmaceutically acceptable carrier.

This invention provides a method of treating an abnormality in a subject wherein the abnormality is alleviated by decreasing the activity of a GALR2 receptor which comprises administering to a subject an effective amount of the above-described pharmaceutical composition, thereby treating the abnormality.

This invention provides a method for identifying an agonist capable of alleviating an abnormality in a subject wherein the abnormality is alleviated by increasing the activity of a GALR2 receptor comprising administering a compound to a transgenic nonhuman mammal and determining whether the compound alleviates the physical and behavioral abnormalities displayed by the transgenic nonhuman mammal, the alleviation of the abnormality identifying the compound as an agonist.

This invention provides an agonist identified by the above-described methods.

This invention provides a pharmaceutical composition comprising an agonist identified by the above-described methods and a pharmaceutically acceptable carrier.

This invention provides a method for treating an abnormality in a subject wherein the abnormality is alleviated by increasing the activity of a GALR2 receptor which comprises administering to a subject an effective amount of the above-described pharmaceutical composition, thereby treating the abnormality.

This invention provides a method for diagnosing a predisposition to a disorder associated with the activity of a specific human GALR2 receptor allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a human GALR2 receptor and labelled with a detectable marker; (e) detecting labelled bands which have hybridized to DNA encoding a human GALR2 receptor labelled with a detectable marker to create a unique band pattern specific to the DNA of subjects suffering from the disorder; (f) preparing DNA obtained for diagnosis by steps a–e; and (g) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

In an embodiment, a disorder associated with the activity of a specific human GALR2 receptor allele is diagnosed. In another embodiment, the above-described method may be used to identify a population of patients having a specific GALR2 receptor allele, in which population the disorder may be alleviated by administering to the subjects a GALR2-selective compound.

This invention provides a method of preparing the purified GALR2 receptor which comprises: (a) inducing cells to express GALR2 receptor; (b) recovering the receptor from the induced cells; and (c) purifying the receptor so recovered.

This invention provides a method of preparing a purified GALR2 receptor which comprises: (a) inserting nucleic acid encoding the GALR2 receptor in a suitable vector; (b) introducing the resulting vector in a suitable host cell; (c) placing the resulting cell in suitable condition permitting the production of the isolated GALR2 receptor; (d) recovering the receptor produced by the resulting cell; and (e) purifying the receptor so recovered.

This invention provides a method of modifying feeding behavior of a subject which comprises administering to the subject an amount of a compound which is a galanin receptor agonist or antagonist effective to increase or decrease the consumption of food by the subject so as to thereby modify feeding behavior of the subject. In an embodiment, the compound is a GALR2 receptor antagonist and the amount is effective to decrease the consumption of food by the subject. In another embodiment the compound is administered in combination with food.

In yet another embodiment the compound is a GALR2 receptor agonist and the amount is effective to increase the consumption of food by the subject. In a still further embodiment, the compound is administered in combination with food. In other embodiments the subject is a vertebrate, a mammal, a human or a canine.

This invention provides a method of treating Alzheimer's disease in a subject which comprises administering to the subject an amount of a compound which is a galanin receptor antagonist effective to treat the subject's Alzheimer's disease. In one embodiment, the galanin receptor antagonist is a GALR2 receptor antagonist and the amount of the compound is effective to treat the subject's Alzheimer's disease.

This invention provides a method of producing analgesia in a subject which comprises administering to the subject an amount of a compound which is a galanin receptor agonist effective to produce analgesia in the subject. In another embodiment, the galanin receptor agonist is a GALR2 receptor agonist and the amount of the compound is effective to produce analgesia in the subject.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

MATERIALS AND METHODS

Construction and screening of a rat hypothalamus cDNA library

Total RNA was prepared from rat hypothalami by a modification of the guanidine thiocyanate method (Chirgwin, 1979). Poly A$^+$ RNA was purified using a Fast-Track kit (Invitrogen Corp., San Diego, Calif.). Double stranded (ds) cDNA was synthesized from 4.6 $\mu$g of poly A$^+$ RNA according to Gubler and Hoffman (1983) with minor modifications. The resulting cDNA was ligated to BstXI/EcoRI adaptors (Invitrogen Corp.) and the excess adaptors removed by exclusion column chromatography. High molecular weight fractions of size-selected ds-cDNA were ligated in pEXJ.T7 (an Okayama and Berg expression vector modified from pcEXV (Miller & Germain, 1986) to contain BstXI and other additional restriction sites and a T7 promoter (Stratagene) and electroporated in E. coli MC 1061 (Gene Pulser, Biorad). A total of 3×10$^6$ independent clones with a mean insert size of 2.2 kb were generated. The library was plated on agar plates (Ampicillin selection) in 584 primary pools of ~5,000 independent clones. After 18 hours amplification, the bacteria from each pool were scraped, resuspended in 4 mL of LB media and 0.75 mL processed for plasmid purification (QIAwell-96 ultra, Qiagen,Inc., Chatsworth, Calif.). Aliquots of each bacterial pool were stored at −85° C. in 20% glycerol.

To screen the library, COS-7 cells were plated in slide chambers (Lab-Tek) in Dulbecco's modified Eagle medium (DMEM) supplemented with 10% calf serum, 100 U/mL of penicillin, 100 µg/mL streptomycin, 2 mM L-glutamine (DMEM-C) and grown at 37° C. in a humidified 5% $CO_2$ atmosphere for 24 hours before transfection. Cells were transfected with miniprep DNA prepared from the primary pools (~4,500 cfu/pool) of the rat hypothalamus cDNA library using a modification of the DEAE-dextran method (Warden & Thorne, 1968). Pools containing GALR1 were identified by PCR prior to screening and were omitted from the primary screen. The galanin binding assay was carried out after 48 hours. Cells were rinsed twice with phosphate-buffered saline (PBS) then incubated with 1 nM 125I-porcine galanin (NEN; specific activity ~2200 Ci/mmol) in 20 mM HEPES-NaOH, pH 7.4, containing 1.26 mM $CaCl_2$, 0.81 mM $MgSO_4$, 0.44 mM $KH_2PO_4$, 5.4 mM KCl, 10 mM NaCl, 0.1% BSA, and 0.1% bacitracin for one hour at room temperature. After rinsing and fixation in 2.5% glutaraldehyde, slides were rinsed in PBS, air-dried, and dipped in photoemulsion (Kodak, NTB-2). After a 3–4 day exposure slides were developed in Kodak D19 developer, fixed, and coverslipped (Aqua-Mount, Lerner Laboratories), then inspected for positive cells by brightfield microscopy (Leitz Laborlux, 25× magnification). One pool with positive cells, (J126) was subdivided and rescreened repeatedly until a single colony was isolated that conferred galanin binding. The 3.8 kb cDNA is preferably sequenced on both strands using Sequenase (US Biochemical, Cleveland, Ohio) according to the manufacturer. Nucleotide and peptide sequence analyses are performed using the Wisconsin Package (GCG, Genetics Computer group, Madison, Wis.) or PC/GENE (Intelligenetics, Mountain View, Calif.).

PCR Methodology

PCR reactions were carried out in 20 µl volumes using Taq Polymerase (Boehringer Mannheim, Indianapolis, Ind.) in a buffer containing 10 mM Tris-HCl, pH 8.3, 50 mM KCl, 1.5 mM $MgCl_2$ 0.01% gelatin, 0.2 mM each dNTP, and 1 µM each PCR primer. To prescreen library pools for GALR1, two GALR1 primer sets were used (KS-1177/1178 and KS-1311/1313, see below) to determine whether GALR1 was present in original bacterial stocks of each library pool. PCR was carried out for 40 cycles of 94° C./2 min, 68° C./2 min, 72° C./3 min. Pools positive for GALR1 by PCR were eliminated from the library screen.

To confirm that the purified cDNA conferring galanin binding was distinct from GALR1, the isolated clone representing pool J126-10-334 (K985) was subjected to PCR analysis using three GALR1 primer sets representing different regions of GALR1. The nucleotide sequences of the primer sets are shown below:

KS-1177: 5'-TGG GCA ACA GCC TAG TGA TCA CCG-3' (Seq. I.D. No. 1) Nucleotides 146–169 of human GALR1 coding region, forward primer.

KS-1178: 5'-CTG CTC CCA GCA GAA GGT CTG GTT-3' (Seq. I.D. No. 2) Nucleotides 547–570 of human GALR1 coding region, reverse primer.

KS-1311: 5'-CCT CAG TGA AGG GAA TGG GAG CGA-3' (Seq. I.D. No. 3) Nucleotides 21–44 of rat GALR1 coding region, forward primer.

KS-1313: 5'-CTC ATT GCA AAC ACG GCA CTT GAA CA-3' (Seq. I.D. No. 4) Nucleotides 944–969 of rat GALR1 coding region, reverse primer.

KS-1447: 5'-CTT GCT TGT ACG CCT TCC GGA AGT-3' (Seq. I.D. No. 5) Nucleotides 920–943 of rat GALR1 coding region, reverse primer.

KS-1448: 5'-GAG AAC TTC ATC ACG CTG GTG GTG-3' (Seq. I.D. No. 6). Nucleotides 91–114 of rat GALR1 coding region, forward primer.

Northern Blots

Human brain multiple tissue northern blots (MTN blots II and III, Clontech, Palo Alto, Calif.) carrying mRNA purified from various human brain areas may be hybridized according to the manufacturers' specifications.

Rat multiple tissue northern blots including multiple brain tissue blots (rat MTN blot, Clontech, Palo Alto, Calif.) carrying mRNA purified from various rat tissues also may be hybridized at high stringency according to the manufacturer's specifications.

RT-PCR analyses of GALR2 mRNA Tissues may be homogenized and total RNA extracted using the guanidine isothiocyanate/CsCl cushion method. RNA may then be treated with DNase to remove any contaminating genomic DNA. cDNA may be prepared from total RNA with random hexanucleotide primers using the reverse transcriptase Superscript II (BRL, Gaithersburg, Md.). First strand cDNA (about 250 ng of total RNA) may be amplified for example, in a 50 µL PCR reaction mixture (200 µM dNTPs final concentration) and 1 µM appropriate primers, using an appropriate thermal cycling program.

The PCR products may be run on a 1.5% agarose gel and transferred to charged nylon membranes (Zetaprobe GT, BioRad), and analyzed as Southern blots. GALR2 primers will be screened for the absence of cross-reactivity with the other galanin receptors. Filters may be hybridized with radiolabeled probes and washed under high stringency. Labeled PCR products may be visualized on X-ray film. Similar PCR and Southern blot analyses may be conducted with primers and probes, e.g., 1B15, directed to the housekeeping gene, glyceraldehyde phosphate dehydrogenase (Clontech, Palo Alto, Calif.), to normalize the amount of cDNA used from the different tissues.

RT PCR of rat brain tissues was carried out using total or poly $A^+$ RNA (1.5 µg or 0.5 µg, respectively) isolated from various rat brain regions and converted to cDNA using Superscript II (BRL, Gaithersburg, Md.) reverse transcriptase with random priming. The cDNAs were used as templates for PCR amplification of GALR2 using specific GALR2 primers. PCR products were separated on an agarose gel by electrophoresis and blotted to a charged nylon membrane.

Production of Recombinant Baculovirus

The coding region of GALR2 may be subcloned into pBlueBacIII into existing restriction sites, or sites engineered into sequences 5' and 3' to the coding region of GALR2, for example, a 5' BamHI site and a 3' EcoRI site. To generate baculovirus, 0.5 µg of viral DNA (BaculoGold) and 3 µg of GALR2 construct may be co-transfected into $2 \times 10^6$ *Spodoptera frugiperda* insect Sf9 cells by the calcium phosphate co-precipitation method, as outlined in by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Cell Culture

COS-7 cells are grown on 150 mm plates in DMEM with supplements (Dulbecco's Modified Eagle Medium with 10% bovine calf serum, 4 mM glutamine, 100 units/mL penicillin/100 μg/mL streptomycin) at 37° C., 5% $CO_2$. Stock plates of COS-7 cells are trypsinized and split 1:6 every 3–4 days. Human embryonic kidney 293 cells are grown on 150 mm plates in D-MEM with supplements (minimal essential medium) with Hanks' salts and supplements (Dulbecco's Modified Eagle Medium with 10% bovine calf serum, 4 mM glutamine, 100 units/mL penicillin/100 μg/mL streptomycin) at 37° C., 5% $CO_2$. Stock plates of 293 cells are trypsinized and split 1:6 every 3–4 days. Mouse fibroblast LM(tk-) cells are grown on 150 mm plates in D-MEM with supplements (Dulbecco's Modified Eagle Medium with 10% bovine calf serum, 4 mM glutamine, 100 units/mL penicillin/100 μg/mL streptomycin) at 37° C., 5% $CO_2$. Stock plates of LM(tk-) cells are trypsinized and split 1:10 every 3–4 days.

LM(tk-) cells stably transfected with the GALR2 receptor may be routinely converted from an adherent monolayer to a viable suspension. Adherent cells are harvested with trypsin at the point of confluence, resuspended in a minimal volume of complete DMEM for a cell count, and further diluted to a concentration of $10^6$ cells/mL in suspension media (10% bovine calf serum, 10% 10× Medium 199 (Gibco), 9 mM $NaHCO_3$, 25 mM glucose, 2 mM L-glutamine, 100 units/mL penicillin/100 μg/mL streptomycin, and 0.05% methyl cellulose). Cell suspensions are maintained in a shaking incubator at 37° C., 5% CO—. for 24 hours. Membranes harvested from cells grown in this manner may be stored as large, uniform batches in liquid nitrogen. Alternatively, cells may be returned to adherent cell culture in complete DMEM by distribution into 96-well microtiter plates coated with poly-D-lysine (0.01 mg/mL) followed by incubation at 37° C., 5% $CO_2$ for 24 hours. Cells prepared in this manner generally yield a robust and reliable response in cAMP radio-immunoassays as further described hereinbelow.

Mouse embryonic fibroblast NIH-3T3 cells are grown on 150 mm plates in Dulbecco's Modified Eagle Medium (DMEM) with supplements (10% bovine calf serum, 4 mM glutamine, 100 units/mL penicillin/100 μg/mL streptomycin) at 37° C., 5% CO2. Stock plates of NIH-3T3 cells are trypsinized and split 1:15 every 3–4 days.

Sf9 and Sf21 cells are grown in monolayers on 150 mm tissue culture dishes in TMN-FH media supplemented with 10% fetal calf serum, at 27° C., no $CO_2$. High Five insect cells are grown on 150 mm tissue culture dishes in Ex-Cell 400™ medium supplemented with L-Glutamine, also at 27° C., no $CO_2$.

Transfection

All receptor subtypes studied may be transiently transfected into COS-7 cells by the DEAE-dextran method, using 1 μg of DNA/$10^6$ cells (Cullen, 1987). In addition, Schneider 2 Drosophila cells may be cotransfected with vectors containing the receptor gene, under control of a promoter which is active in insect cells, and a selectable resistance gene, eg., the G418 resistant neomycin gene, for expression of the galanin receptor.

Stable Transfection

The GALR2 receptor may be co-transfected with a G-418 resistant gene into the human embryonic kidney 293 cell line by a calcium phosphate transfection method (Cullen, 1987). Stably transfected cells are selected with G-418. GALR2 receptors may be similarly transfected into mouse fibroblast LM(tk-) cells, Chinese hamster ovary (CHO) cells and NIH-3T3 cells. Transfection of LM(tk-) cells with the plasmid K985 and subsequent selection with G-418 resulted in the LM(tk-) cell line L-rGALR2-8 (ATCC Accession No. CRL-12074), which stably expresses the rat GALR2 receptor.

Radioligand binding assays

Transfected cells from culture flasks were scraped into 5 ml of Tris-HCl, 5 mM EDTA, pH 7.5, and lysed by sonication. The cell lysates were centrifuged at 1000 rpm for 5 min. at 4° C., and the supernatant was centrifuged at 30,000×g for 20 min. at 4° C. The pellet was suspended in binding buffer (50 mM Tris-HCl, 5 MM $MgSO_4$, 1 mM EDTA, 100 mM NaCl at pH 7.5 supplemented with 0.1% BSA, 2 μg/ml aprotinin, 0.5 mg/ml leupeptin, and 10 μg/ml phosphoramidon). Optimal membrane suspension dilutions, defined as the protein concentration required to bind less than 10% of the added radioligand, were added to 96-well polpropylene microtiter plates containing $^{125}$I-labeled peptide, non-labeled peptides and binding buffer to a final volume of 250 μl. In equilibrium saturation binding assays membrane preparations were incubated in the presence of increasing concentrations (0.1 nM to 4 nM) of [$^{125}$I]porcine galanin (specific activity 2200 Ci/mmol). The binding affinities of the different galanin analogs were determined in equilibrium competition binding assays, using 0.1 nM [$^{125}$I] porcine galanin in the presence of twelve different concentrations of the displacing ligands. Binding reaction mixtures were incubated for 1 hr at 30° C., and the reaction was stopped by filtration through GF/B filters treated with 0.5% polyethyleneimine, using a cell harvester. Radioactivity was measured by scintillation counting and data were analyzed by a computerized non-linear regression program. Non-specific binding was defined as the amount of radioactivity remaining after incubation of membrane protein in the presence of 100 nM of unlabeled porcine galanin. Protein concentration was measured by the Bradford method using Bio-Rad Reagent, with bovine serum albumin as a standard.

Functional Assays

The receptor-mediated inhibition of cyclic AMP (cAMP) formation may be assayed in LM(tk-) cells expressing the rat GALR1 and GALR2 receptors. Cells were plated in 96well plates and incubated in Dulbecco's phosphate buffered saline (PBS) supplemented with 10 mM HEPES, 5 mM theophylline, 2 μg/ml aprotinin, 0.5 mg/ml leupeptin, and 10 μg/ml phosphoramidon for 20 min at 37° C., in 5% $CO_2$. Galanin or the test compounds were added and incubated for an additional 10 min at 37° C. The medium was aspirated and the reaction was stopped by the addition of 100 mM HCl. The plates were stored at 4° C. for 15 min, and the cAMP content in the stopping solution was measured by radioimmunoassay. Radioactivity was quantified using a gamma counter equipped with data reduction software.

Functional Assay: Intracellular calcium mobilization

The intracellular free calcium concentration may be measured by microspectroflourometry using the fluorescent indicator dye Fura-2/AM (Bush et al. 1991). Stably transfected cells are seeded onto a 35 mm culture dish containing a glass coverslip insert. Cells are washed with HBS and loaded with 100 μL of Fura-2/AM (10 μM) for 20 to 40 min. After washing with HBS to remove the Fura-2/AM solution, cells are equilibrated in HBS for 10 to 20 min. Cells are then visualized under the 40X objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

Functional Assay: Phosphoinositide metabolism

LM(tk-) cells stably expressing the rat GALR2 receptor cDNA were plated in 96-well plates and grown to confluence. The day before the assay the growth medium was changed to 100 µl of medium containing 1% serum and 0.5 µCi [$^3$H]myo-inositol, and the plates were incubated overnight in a $CO_2$ incubator (5% $CO_2$ at 37° C.). Immediately before the assay, the medium was removed and replaced by 200 µL of PBS containing 10 mM LiCl, and the cells were equilibrated with the new medium for 20 min. During this interval cells were also equilibrated with the antagonist, added as a 10 µL aliquot of a 20-fold concentrated solution in PBS. The [$^3$H]inositol-phosphates accumulation from inositol phospholipid metabolism was started by adding 10 µL of a solution containing the agonist. To the first well 10 µL were added to measure basal accumulation, and 11 different concentrations of agonist were assayed in the following 11 wells of each plate row. All assays were performed in duplicate by repeating the same additions in two consecutive plate rows. The plates were incubated in a CO incubator for 1 hr. The reaction was terminated by adding 15 µl of 50% v/v trichloroacetic acid (TCA), followed by a 40 min. incubation at 4° C. After neutralizing TCA with 40 µl of 1M Tris, the content of the wells was transferred to a Multiscreen HV filter plate (Millipore) containing Dowex AG1-X8 (200–400 mesh, formate form). The filter plates were prepared adding 200 µL of Dowex AG1-X8 suspension (50% v/v, water: resin) to each well. The filter plates were placed on a vacuum manifold to wash or elute the resin bed. Each well was washed 2 times with 200 µL of water, followed by 2×200 µL of 5 mM sodium tetraborate/60 mM ammonium formate. The [$^3$H]IPs were eluted into empty 96-well plates with 200 µl of 1.2M ammonium formate/0.1 formic acid. The content of the wells was added to 3 mls of scintillation cocktail, and the radioactivity was determined by liquid scintillation counting.

Galanin Receptor Autoradiography

Male Sprague-Dawley rats (Charles River) were euthanized using $CO_2$, decapitated, and their brains immediately removed and frozen on dry ice. Tissue sections were cut at 20 µm using a cryostat and thaw mounted onto gelatin coated slides. Tissues were preincubated in two 10 minute changes of 50 mM Tris-HCl buffer pH 7.4, containing 5 mM $MgSO_4$ and 2 mM EGTA (Sigma). The radioligand binding was carried out in the same buffer, which also contained 0.1% bovine serum albumin, 0.02% aprotinin, 0.031% leupeptin, 0.1% phosphoramidate (Boehringer Mannheim), and 0.1 nM [$^{125}$I]porcine galanin (specific activity 2200 Ci/mmol, NEN) for 1 hour at 22° C. Nonspecific binding was determined in the presence of 5 µM porcine galanin (Bachem). As [D-Trp2]galanin$_{(1-29)}$ was shown to be selective for the cloned GALR2 receptor (infra), a 60 nM concentration of this peptide was used to displace [$^{125}$I] galanin binding from the rat brain tissue sections. The use of this concentration was based on the binding data, which showed the affinity of [D-Trp$^2$]galanin$_{(1-29)}$ to be 6 nM at the GALR2 receptor, and 3 µM at the GALR1 receptor. In general, a 10× concentration of the blocking ligand is sufficient to remove 100% of the targeted receptor, while leaving the GALR1 receptor unaffected. After incubation, tissues were dipped twice in ice-cold Tris-HCl buffer (4° C.), followed by a 5 minute wash in ice-cold Tris-HCl buffer (4° C.), then dipped twice in ice-cold deionized water to remove the salts. Sections were placed in X-ray cassettes and apposed to Dupont Cronex MRF 34 Film for 5 days. Films were developed using a Kodak M35A Processor.

Tissue preparation for neuroanatomical studies

Male Sprague-Dawley rats (Charles River) are decapitated and the brains rapidly removed and frozen in isopentane. Coronal sections are cut at 11 µm on a cryostat and thaw-mounted onto poly-L-lysine coated slides and stored at −80° C. until use. Prior to hybridization, tissues are fixed in 4% paraformaldehyde, treated with 5 mM dithiothreitol, acetylated in 0.1 M triethanolamine containing 0.25% acetic anhydride, delipidated with chloroform, and dehydrated in graded ethanols.

Probes

Oligonucleotide probes employed to characterize the distribution of the rat GALR2 receptor mRNA may be synthesized, for example, on a Millipore Expedite 8909 Nucleic Acid Synthesis System. The probes are then lyophilized, reconstituted in sterile water, and purified on a 12% polyacrylamide denaturing gel. The purified probes are again reconstituted to a concentration of 100 ng/µL, and stored at −20° C. Probe sequences may include DNA or RNA which is complementary to the mRNA which encodes the GALR2 receptor.

In Situ Hybridization

Probes are 3'-end labeled with $^{35}$S-DATP (1200 Ci/mmol, New England Nuclear, Boston, Mass.) to a specific activity of about $10^9$ dpm/µg using terminal deoxynucleotidyl transferase (Pharmacia). The radiolabeled probes are purified on Biospin 6 chromatography columns (Bio-Rad; Richmond, Calif.), and diluted in hybridization buffer to a concentration of $1.5\times10^4$ cpm/µL. The hybridization buffer consists of 50% formamide, 4× sodium citrate buffer (1× SSC=0.15M NaCl and 0.015M sodium citrate), 1× Denhardt's solution (0.2% polyvinylpyrrolidine, 0.2% Ficoll, 0.2% bovine serum albumin), 50 mM dithiothreitol, 0.5 mg/ml salmon sperm DNA, 0.5 mg/ml yeast tRNA, and 10% dextran sulfate. About one hundred µL of the diluted radiolabeled probe is applied to each section, which is then covered with a Parafilm coverslip. Hybridization is carried out overnight in humid chambers at 40 to 55° C. The following day the sections are washed in two changes of 2× SSC for one hour at room temperature, in 2× SSC for 30 min at 50–60° C., and finally in 0.1× SSC for 30 min at room temperature. Tissues are dehydrated in graded ethanols and apposed to Kodak XAR-5 film for 3 days to 3 weeks at −20° C., then dipped in Kodak NTB3 autoradiography emulsion diluted 1:1 with 0.2% glycerol water. After exposure at 4° C. for 2 to 8 weeks, the slides are developed in Kodak D-19 developer, fixed, and counterstained with cresyl violet.

In vivo methods

In order to determine whether a compound is a GALR2 antagonist, food intake in rats may be stimulated by administration of the GALR2-selective peptide aonist [D-Trp$_2$]-galanin$_{(1-29)}$ through an intracerebroventricular (i.c.v.) cannula. A preferred anatomic location for injection is the hypothalamus, in particular, the paraventricular nucleus. Methods of cannulation and food intake measurements are well-known in the art, as are i.c.v. modes of administration (Kyrkouli et al., 1990, Ogren et al., 1992). To determine whether a compound reduces [D-Trp$_2$]-galanin$_{(1-29)}$ stimulated food intake, the compound may be administered either simultaneously with the peptide, or separately, either through cannula, or by subcutaneous, intramuscular, or intraperitoneal injection, or more preferably, orally.

Materials

Cell culture media and supplements are from Specialty Media (Lavallette, N.J.). Cell culture plates (150 mm and 96-well microtiter) are from Corning (Corning, N.Y.). Sf9, Sf21, and High Five insect cells, as well as the baculovirus transfer plasmid, pBlueBacIII™, are purchased from Invitrogen (San Diego, Calif.). TMN-FH insect medium complemented with 10% fetal calf serum, and the baculovirus DNA, BaculoGold™, is obtained from Pharmingen (San Diego, Calif.). Ex-Cell 400™ medium with L-Glutamine is purchased from JRH Scientific. Polypropylene 96-well microtiter plates are from Co-star (Cambridge, Mass.). All radioligands are from New England Nuclear (Boston, Mass.).

Galanin and related peptide analogs were either from Bachem California (Torrance, Calif.), Peninsula (Belmont, Calif.); or were synthesized by custom order from Chiron Mimotopes Peptide Systems (San Diego, Calif.).

Bio-Rad Reagent was from Bio-Rad (Hercules, Calif.). Bovine serum albumin (ultra-fat free, A-7511) was from Sigma (St. Louis. Mo.). All other materials were reagent grade.

EXPERIMENTAL RESULTS

Isolation of a GALR2 cDNA from rat hypothalamus

In order to clone additional members of the galanin receptor family, we designed an expression cloning strategy based on the potential presence of multiple galanin receptors in hypothalamus. Although recent evidence indicated that GALR1 receptor mRNA was present in rat hypothalamus (Gustafson et al., in press; Parker et al., in press), not all aspects of the cloned GALR1 pharmacological profile match that observed for galanin-mediated feeding (Crawley et al., 1993). These results suggested that the regulation of galanin-induced feeding may not be explained by the presence of only GALR1 in the rat hypothalamus.

A randomly-primed cDNA expression library was constructed from rat hypothalamus and screened by radioligand binding/photoemulsion detection using [$^{125}$I]-porcine galanin. The library consisted of 584 pools containing about 5,000 primary clones/pool for a total of about 3 million clones with an average insert size of 2.2 kb. Pools positive for rat GALR1 (about 110) were eliminated from the screen. Remaining pools were screened for radioligand binding using 1 nM [$^{125}$I]-porcine galanin; slides were inspected for positive cells by direct microscopic examination. One positive pool (J126) was subdivided into 96 pools of about 90 clones each and rescreened for galanin binding. Preliminary pharmacology carried out on the positive subpool J126-10 indicated that the [$^{125}$I]-porcine galanin binding was not sensitive to inhibition by galanin 3-29. 400 individual colonies of a positive pool (J26-10) were then screened to find two single purified cDNA clones. J126-10-334 was chosen for further analysis and designated K985. PCR analysis using three independent GALR1 primer sets (see Methods; data not shown) confirmed that the newly isolated cDNA was distinct from GALR1 and thus encoded a new galanin receptor subtype, termed GALR2.

The isolated clone K985 carries a 3.8 kb insert. Sequence analysis of this cDNA revealed a complete coding region for a novel receptor protein which we term GALR2 (see FIGS. 1 and 2). Searches of GenEMBL databases indicated that the sequence was novel, and that the most similar sequence was that of the galanin receptor GALR1, followed by other G protein-coupled receptors (GPCR). The nucleotide and deduced amino acid sequences are shown in FIGS. 1 and 2, respectively. The nucleotide sequence of the coding region is ~56% identical to rat GALR1 and ~54% identical to human GALR1 and encodes a 372 amino acid protein with 38% and 40% amino acid identity to rat and human GALR1, respectively. Hydropathy plots of the predicted amino acid sequence reveal seven hydrophobic regions that may represent transmembrane domains (TMs, data not shown), typical of the G protein-coupled receptor superfamily. In the putative TM domains, GALR2 exhibits 48–49% amino acid identity with rat and human GALR1. Like most GPCRs, the GALR2 receptor contains consensus sequences for N-linked glycosylation in the N-terminus (positions 2 and 11) as well as the predicted extracellular loop between TMs IV and V. The GALR2 receptor contains two highly conserved cysteine residues in the first two extracellular loops that are believed to form a disulfide bond stabilizing the functional protein structure (Probst et al., 1992). GALR2 shows five potential phosphorylation sites for protein kinase C in positions 138, 210, 227, 319, and 364, and two cAMP- and cGMP-dependent protein kinase phosphorylation sites in positions 232 and 316. It should be noted that six out of the seven potential phosphorylation sites are located in predicted intracellular domains, and therefore could play a role in regulating functional characteristics of the GALR2 receptor (Probst et al., 1992).

Figure 3B:
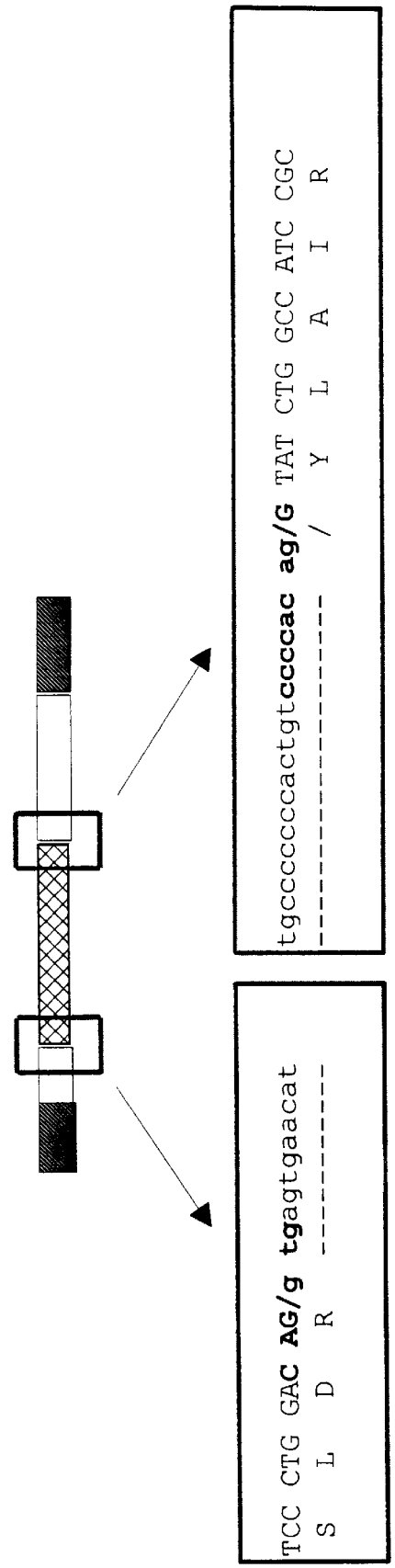

Within the GALR2 cDNA K985 (J126-10-334) isolated from the rat hypothalamus library, the coding region of GALR2 is interrupted by an intron of ~1 kb (FIGS. 3A, 3B, and 3C). A cDNA containing an intron may be produced by the action of reverse transcriptase on an incompletely spliced form of messenger RNA. The heterologous expression of the complete protein product is not necessarily impeded by the presence of the intron in the coding region, because the intron can typically be spliced out prior to translation by the host cell machinery. In the case of the GALR2 cDNA, the location of the intron combined with clear consensus sequences for 5' and 3' splice junctions (FIGS. 3A and 3B) confirm that the intervening sequence represents an intron. As shown in FIG. 3C, splicing of the intron at the indicated sites recreates an open reading frame within a highly conserved region of the GPCR family, at the end of TMIII (LDR/Y). It is of interest to note that several GPCRs have previously been reported to contain introns at this location, including the human dopamine D3, D4, and D5 receptors, the rat substance P receptor, and the human substance K receptor (Probst et al., 1992). In particular, the rat 5-HT$_7$ receptor (Shen et al., 1993) contains an intron in exactly the same location as we now report for GALR2, within the AG/G codon for the highly conserved amino acid arginine at the end of TMIII (FIG. 3C).

To explore the possibility that incompletely or alternately spliced forms GALR2 mRNAs are present in the rat brain, we carried out RT-PCR using GALR2 PCR primers that are located in the coding region but that span the location of the intron. The sequences of the PCR primers are:

KS-1515 (Forward primer): 5'-CAAGGCTGTTCATTTCCTCATCTTTC (loop between TMs II and III)(SEQ. ID No. 12)

KS-1499 (Reverse primer): 5'-TTGGAGACCAGAGCGTAAACGATGG (end of TMVII)(SEQ. ID No. 13)

The PCR products were separated by gel electrophoresis, blotted, and hybridized with a radiolabeled oligonucleotide probe representing the predicted loop between TMs V and VI. The sequence of the oligonucleotide is:

KS-1540: 5'-AGTCGACCCGGTGACTGCAGGCTCAGGTTCCCAGCGCGCCAAACG (SEQ. ID No. 14)

Figures 4, 4A, 5:
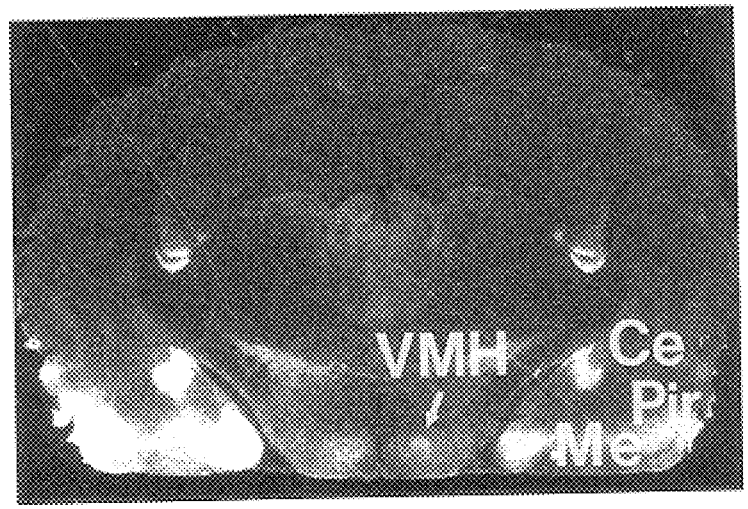
Figures 4, 4A, 5, 6:
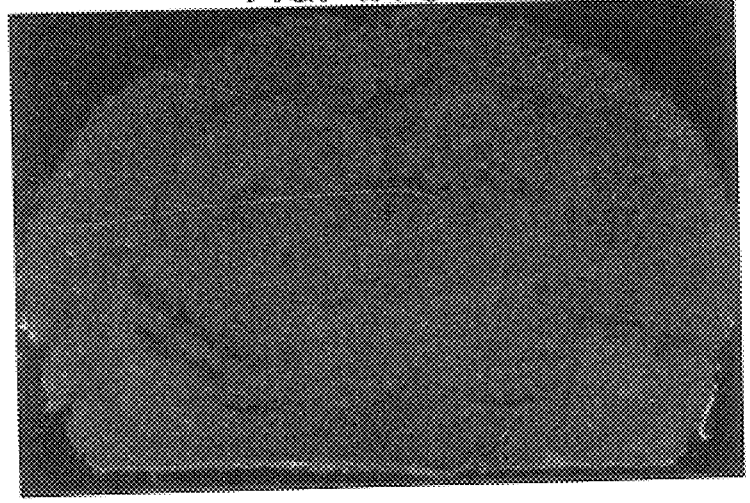
Figures 1, 4B:
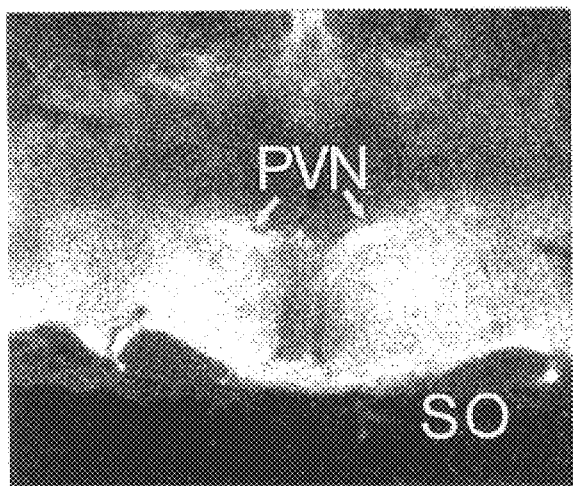
Figures 2, 4B:
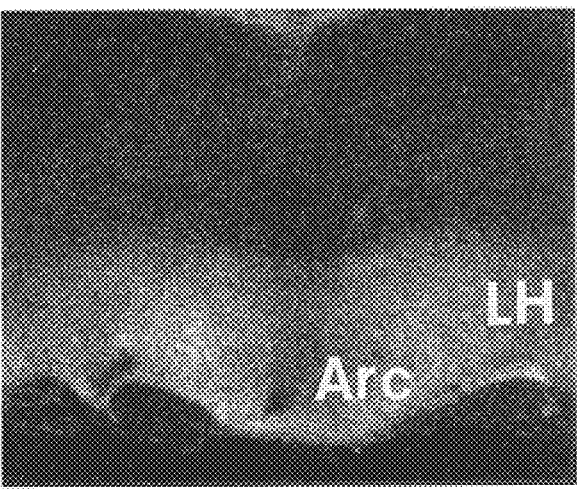
Figures 3, 4B:
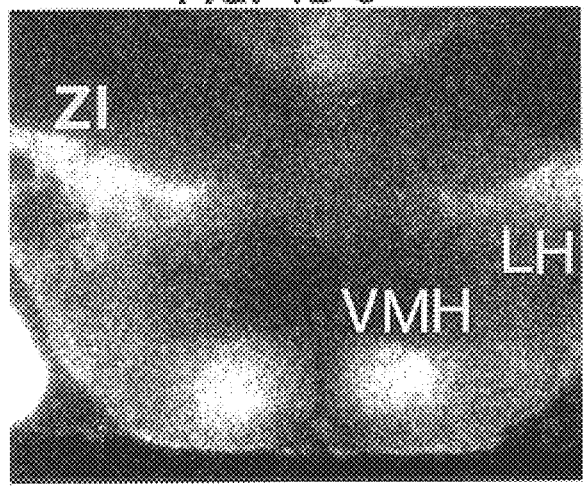
Figures 4, 4B:
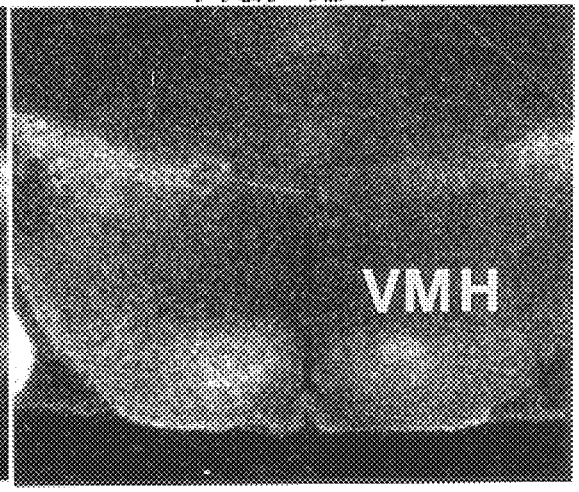
Figures 4, 4B, 5:
Figures 4, 4B, 5, 6:
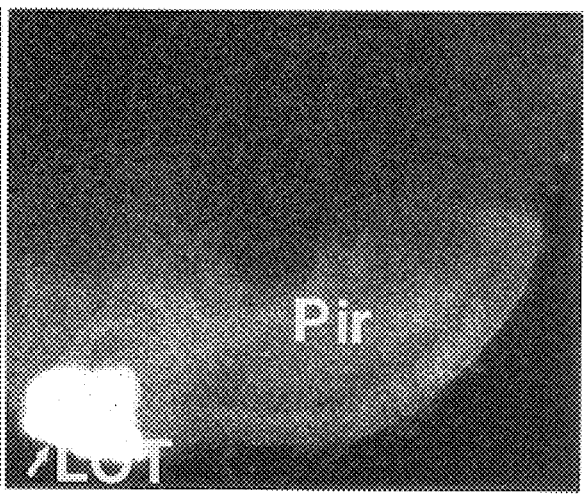
Figures 4, 4B, 5, 6, 7:
Figures 4, 4B, 5, 6, 7, 8:
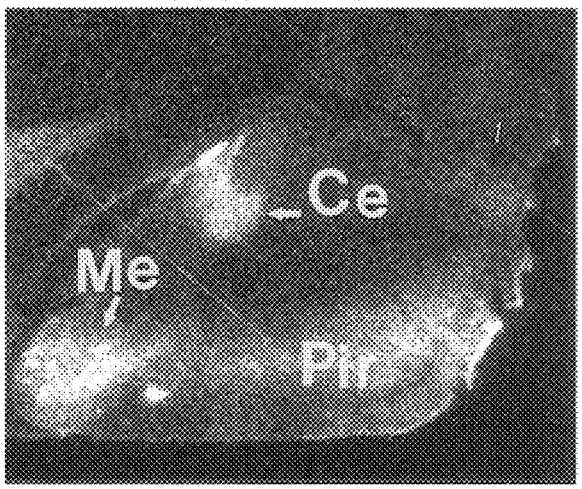
Figures 1, 4C:
Figures 2, 4C:
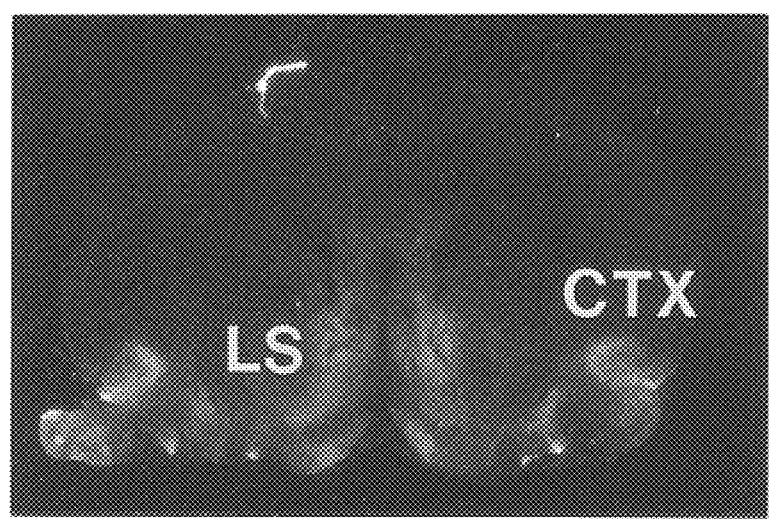
Figures 3, 4C:
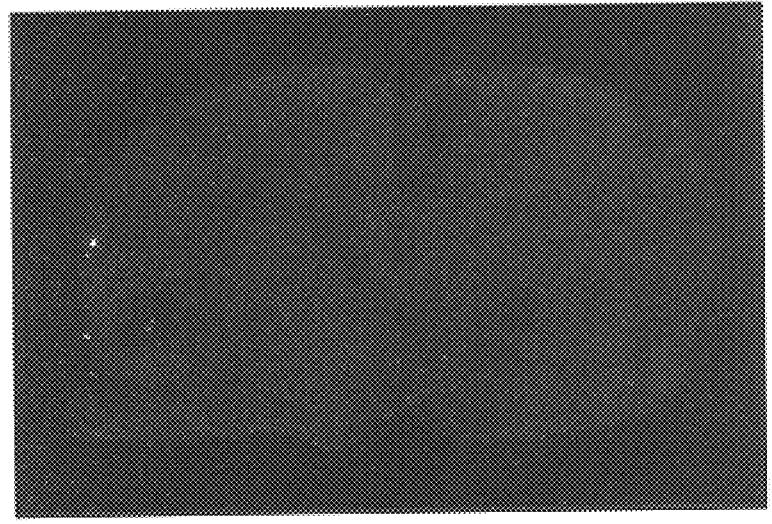
Figures 4, 4C:
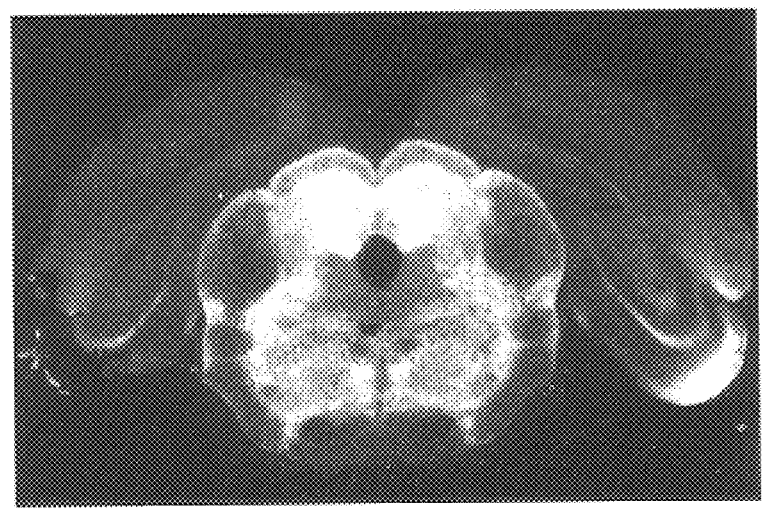
Figures 4, 4C, 5:
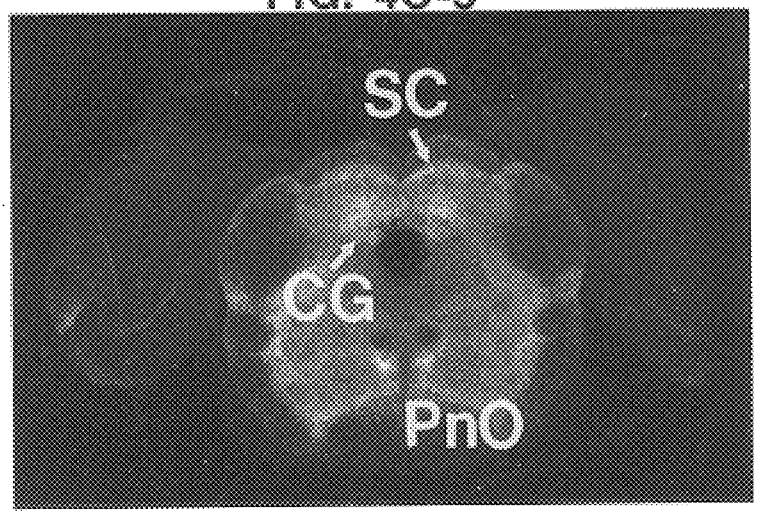
Figures 4, 4C, 5, 6:
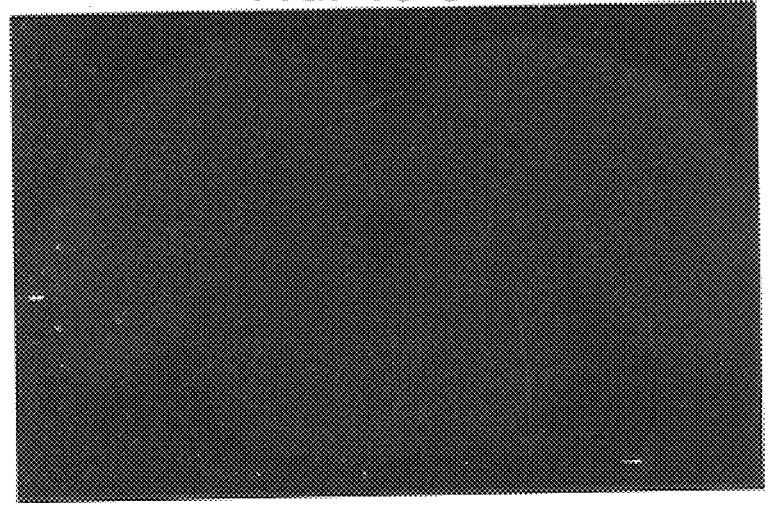
Figure 5:
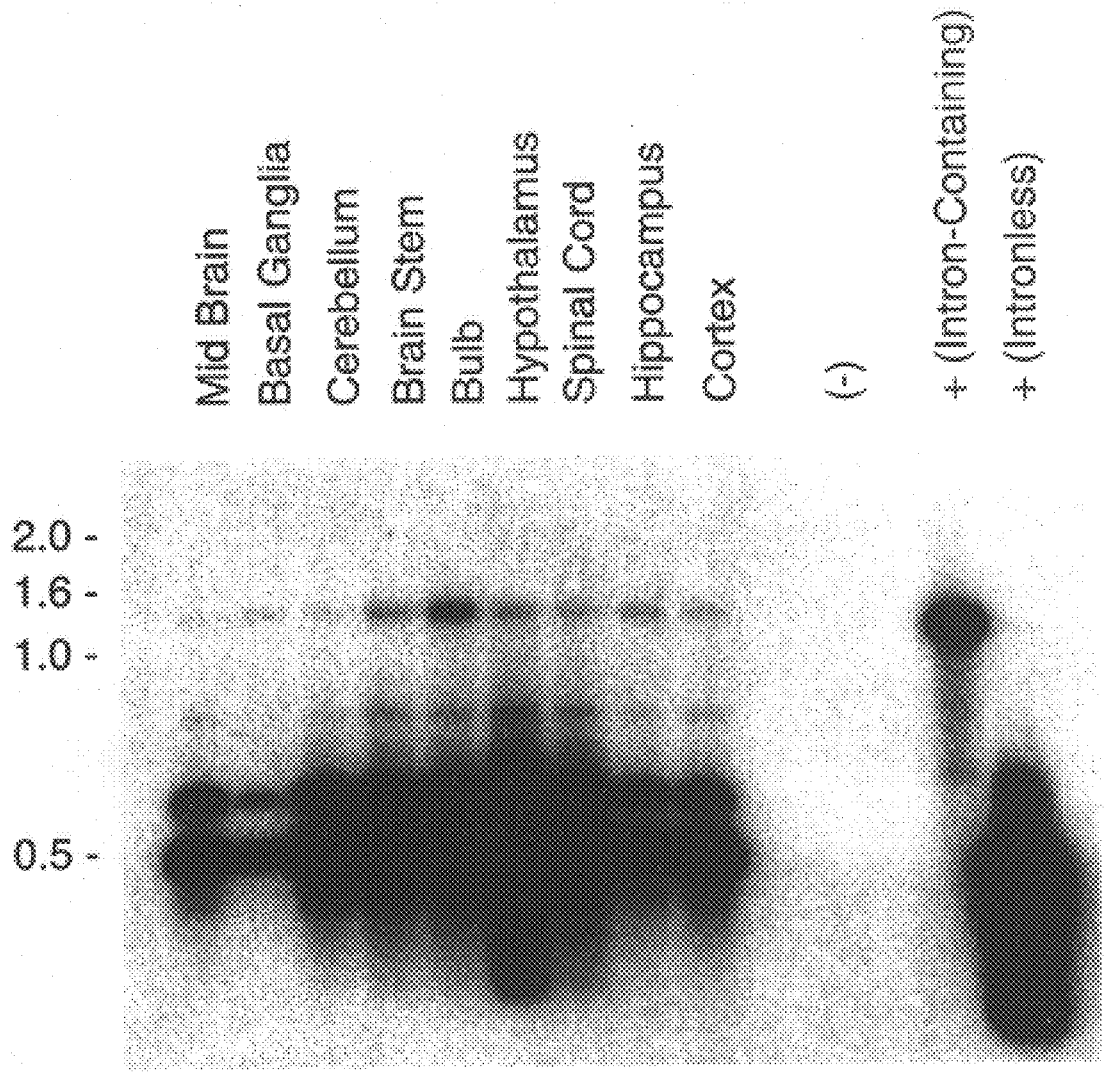

RT-PCR analysis of GALR2 mRNA from various rat brain regions as described above indicates the existence of PCR products that may represent both the intronless (spliced) and intron-containing (incompletely spliced) forms of GALR2 (FIG. 5). In addition, PCR products intermediate in size between intronless and intron-containing products that hybridize at high stringency with the GALR2 oligonucleotide probe KS-1540 are present and may represent additional variations in the GALR2 mRNA. One mechanism that could generate such variations is alternative splicing.

Northern Blot Analysis of GALR2 mRNA

Figure 6A:
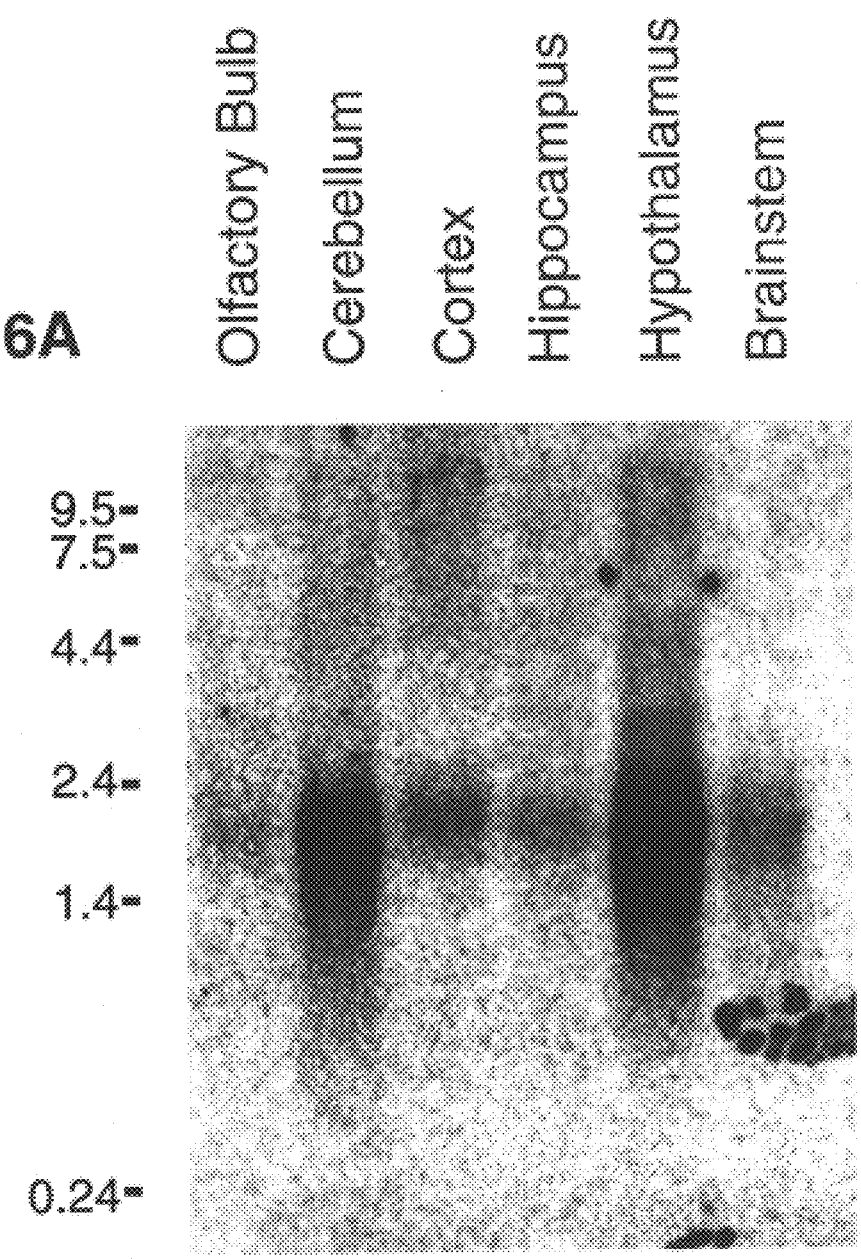
FIGS. 6A–6B. Northern blot analysis of GALR2 receptor mRNA from various rat brain regions. 6A. A Northern blot containing poly A$^+$ RNA (~5 μg) from six different rat brain regions was hybridized at high stringency with a randomly primed radiolabeled fragment representing the entire rat GALR2 coding region (not including the intron). The autoradiogram represents a four day exposure and reveals a ~1.8–2.0 kb transcript. 6B. The blot was reprobed with 1B15 (~1 kb) to confirm that similar amounts of RNA were present in each lane.
Figure 6B:
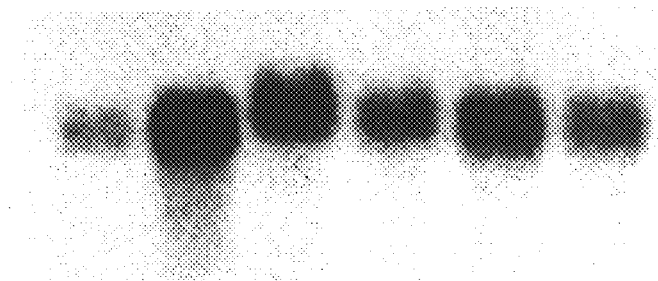
Figure 7A:
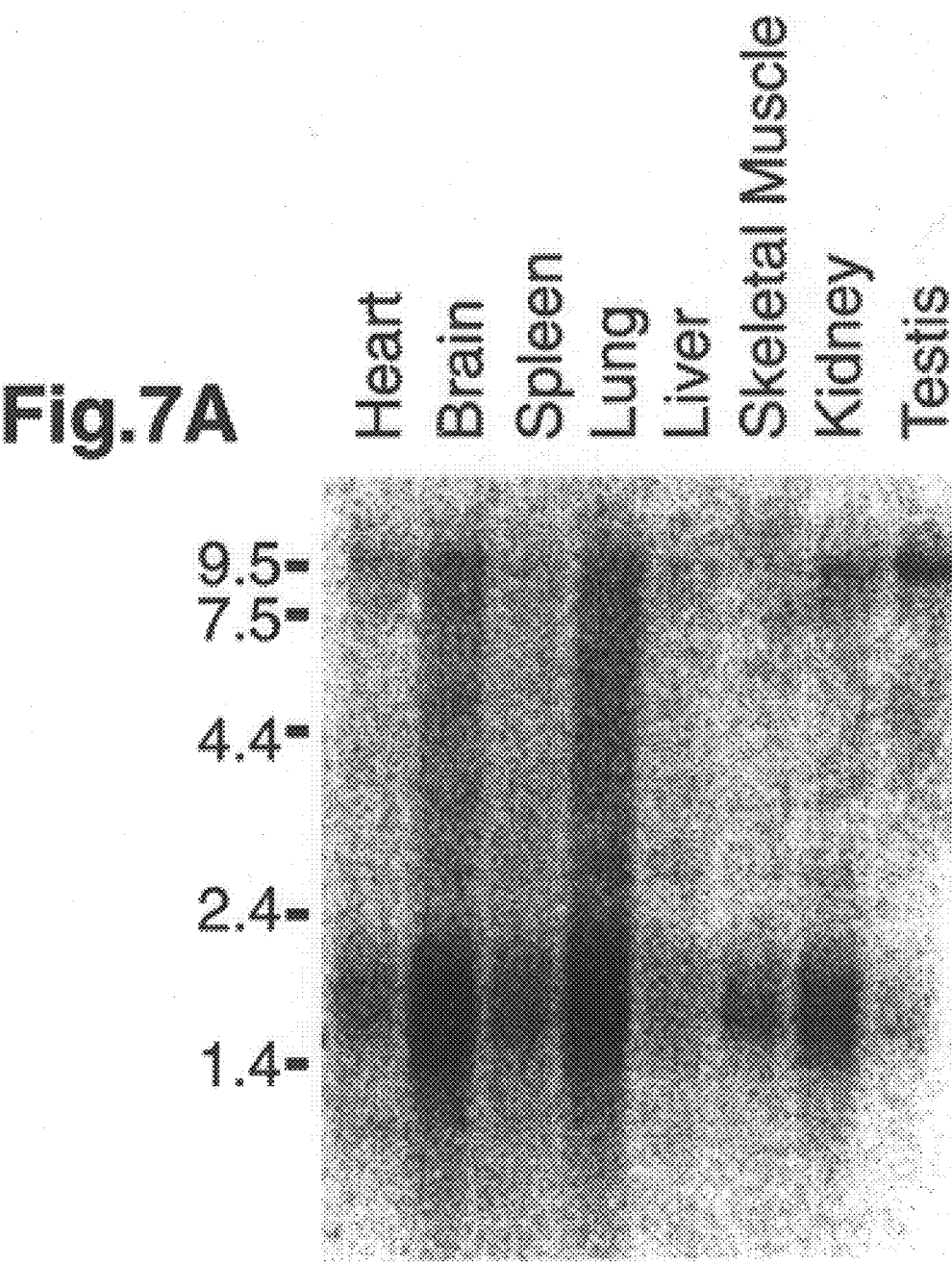
FIGS. 7A–7B. Northern blot analysis of GALR2 receptor mRNA from various rat tissues. 7A. A Northern blot containing poly A$^+$ RNA (~2 μg) from eight different rat tissues was hybridized at high stringency with a randomly primed radiolabeled fragment representing the entire rat GALR2 coding region (not including the intron). The autoradiogram represents a four day exposure and reveals a single ~1.8–2.0 kb transcript. 7B. The Northern blot was reprobed for 1B15 (~1 kb) to confirm that similar amounts of RNA were present in each lane. A second Northern blot (not shown) was also hybridized under the same conditions and showed similar results (Table 3).
Figure 7B:
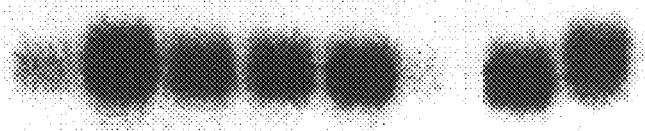
Figure 8A:
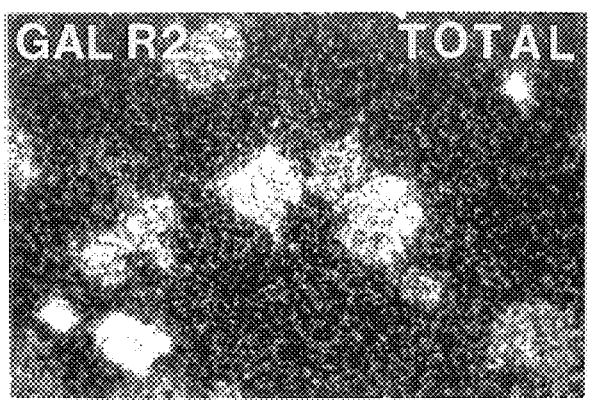
FIGS. 8A–8D. Rat GALR2 receptor autoradiography in COS-7 cells transfected with GALR1 and GALR2 cDNAs. $^{125}$I-[D-Trp$^2$]Galanin$_{(1-29)}$ was tested as a selective radioligand for GALR2. Panels represent dark-field photomicrographs (200x) of photoemulsion-dipped slides. 8A: Binding of 3 nM $^{125}$-[D-Trp$^2$]Galanin$_{(1-29)}$ to COS-7 cells transiently transfected with GALR2. Note positive binding to cells. 8B: Nonspecific binding of 6 nM $^{125}$I-[D-Trp$^2$]Galanin$_{(1-29)}$ in the presence of 300 nM porcine galanin$_{(1-29)}$ to COS-7 cells transiently transfected with GALR2. 8C: Binding of 6 nM $^{125}$I-[D-Trp$^2$]Galanin$_{(1-29)}$ to COS-7 cells transiently transfected with GALR1. Note absence of binding to cell profiles; small accumulations of silver grains represent nonspecific nuclear association. 8D: Nonspecific binding of 6 nM $^{125}$I-[D-Trp$^2$]Galanin$_{(1-29)}$ in the presence of 600 nM porcine galanin$_{(1-29)}$ to COS-7 cells transiently transfected with GALR1.
Figure 8B:
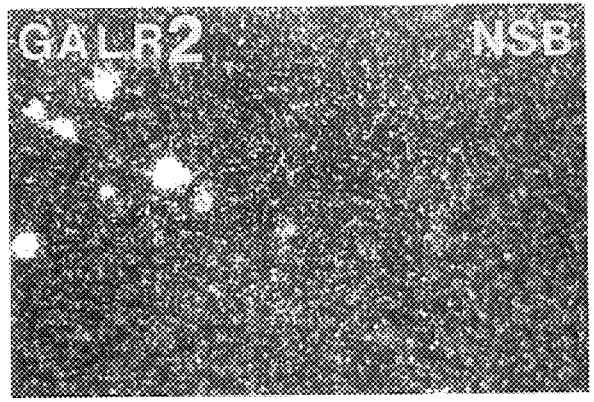
Figure 8C:
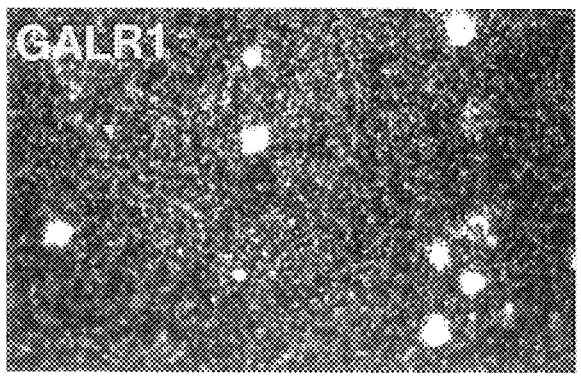
Figure 8D:
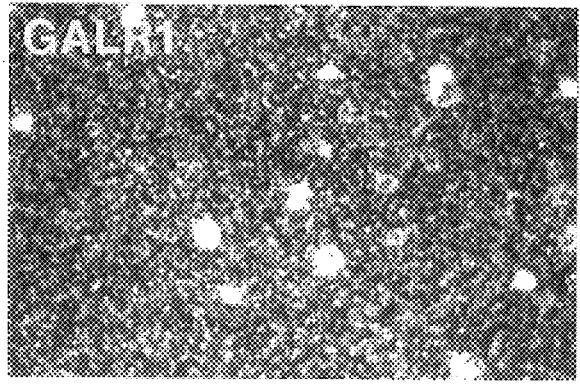

To define the size and distribution of the mRNA encoding GALR2 we carried out Northern blot analysis of poly $A^+$ RNA from various rat tissues and brain regions. A ~1.2 kb fragment of rat GALR2 containing the entire coding region but not containing the intron (FIG. 1) was radiolabeled by random priming and used as a hybridization probe. Northern blots containing rat poly $A^+$ RNA were hybridized at high stringency and apposed to film. A single transcript of ~1.8–2.0 kb is detected after a 4 day exposure of the autoradiogram at −80° C. using Kodak Biomax MS film with one Biomax MS intensifying screen. Within the brain, the highest levels of GALR2 mRNA appear in hypothalamus (FIG. 6A). Among various rat tissues, the GALR2 transcript is widely but unevenly distributed: GALR2 mRNA is observed in brain, lung, heart, spleen, and kidney, with lighter bands in skeletal muscle, liver, and testis (FIG. 7A). Both Northern blots were reprobed with 1B15 to confirm that similar amounts of mRNA were present in each lane (FIGS. 6B and 7B).

Pharmacoloaical characterization of GALR2

The pharmacology of GALR2 was studied in COS-7 cells transiently transfected with the GALR2 cDNA, K985. Membrane preparations of Cos-7 cells transfected with K985 displayed specific binding to [125I]porcine galanin. Scatchard analysis of equilibrium saturation binding data yielded a $K_d$=150 pM with a $B_{max}$=250 fmol/mg protein. The pharmacological properties of the protein encoded by the GALR2 cDNA were probed by measuring the binding affinities of a series of galanin anologs, and compared to those of the rat GALR1 receptor expressed in the same host cell line. As shown in Table 1, both GALR1 and GALR2 receptors showed a high affinity for galanin$_{(1-29)}$, the physiological ligand of these receptors. Both receptors also displayed high affinity for the truncated analogs galanin$_{(1-16)}$ and galanin$_{(1-15)}$. Furthermore, the binding of [$^{125}$I]porcine galanin to either GALR1 or GALR2 at concentrations up to 100 µM was not displaced by porcine galanin$_{(3-29)}$. However, the GALR2 receptor has 540- and 4200-fold higher affinity for [D-Trp$^2$]porcine galanin$_{(1-29)}$, and [D-Trp$^2$]galanin$_{(1-16)}$, respectively, than the GALR1 subtype. Also, [Ala$^5$]galanin$_{(1-6)}$, and [Phe$^2$]galanin$_{(1-15)}$, were moderately selective, with 15- and 17-fold greater affinities for the GALR2 receptor than for the GALR1 receptor subtype, respectively. [Ala$^9$]galanin$_{(1-16)}$ was the only analog that was found to have the opposite selectivity, with 70-fold higher affinity for the GALR1 receptor than for the GALR2 receptor. Interestingly, these two receptor subtypes showed no significant differences in their binding affinities for the chimeric galanin antagonists, galantide, C7, M32, M35, and M40.

Figure 9A:
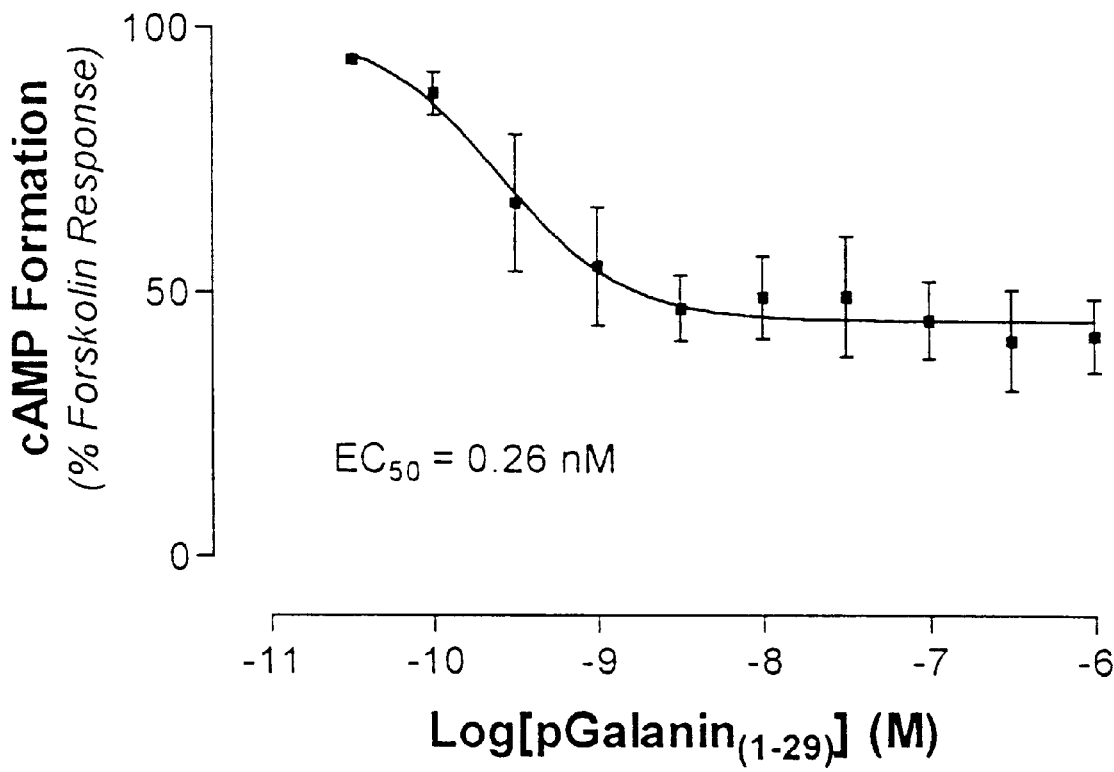
FIGS. 9A–9B. Functional response mediated by LM(tk-) cells stably transfected with the cDNA encoding the rat GALR2 receptor. 9A: Inhibition of cyclic AMP formation: cells were incubated with varying concentrations of porcine galanin$_{(1-29)}$, and 10 $\mu\mu$M forskolin for 15 min. at 37° C. Data was normalized taking as 0% the basal levels of cyclic AMP (0.06±0.02 $\mu$mol/ml) and 100% the cAMP levels produced by forskolin in the absence of agonist (0.26±0.03 pmol/ml). Data is shown as mean±standard error of the mean of four independent experiments. 9B: Phosphoinositide metabolism: cells were incubated for 18 hours in the presence of 0.5 $\mu$Ci [$^3$H]myo-inositol. Eleven different concentrations of porcine galanin$_{(1-29)}$ were added in the presence on 10 mM LiCl. Cells were incubated for 1 hour at 37° C., and [$^3$H]inositol phosphates were isolated and measured.
Figure 9B:
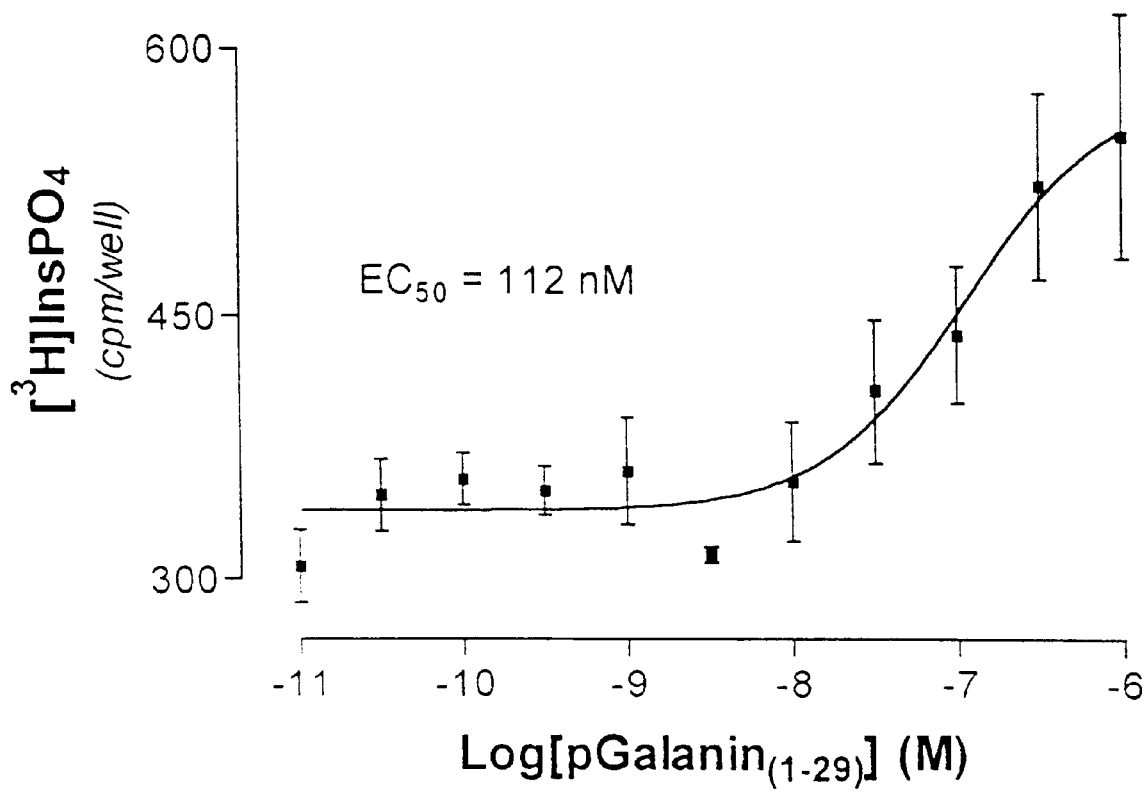

In LM(tk-) cells stably expressing the rat GALR2 receptor cDNA, porcine galanin$_{(1-29)}$ was found to inhibit the formation of cyclic AMP induced by 10 µM forskolin. The effects of galanin were dose dependent with an EC$_{50}$= 0.26±0.13 nM (n=3) (FIG. 9A). In the same cell line porcine galanin$_{(1-29)}$ stimulated the formation of [$^3$H]inositol phosphates, with an EC$_{50}$ =112 nM (FIG. 9B). The phosphoinositide response mediated by the rat. GALR2 receptor suggests that this receptor can also couple to the intracellular calcium mobilization and diacylglycerol pathway. However, the 400-fold lower EC 50 of porcine galanin $_{(1-29)}$ suggests that the GALR2 receptor couples with low efficiency to this signaling pathway. In support of this notion stands the observation that porcine galanin$_{(1-29)}$ had no effect on intracellular calcium levels in COS-7 cells transfected with the cDNA encoding the rat GALR2 receptor. Thus, our data suggest that the GALR2 receptor couples preferentially to $G_{ialpha}$, since the stimulation of phosphoinositide metabolism and intracllular calcium mobilization are a hallmark or receptors to the $G_{qa}$ family of G-proteins. Furthermore, our date also indicate that the inhibition of cAMP formation, as well as the stimulation of phosphoinositide metabolism, can be used as functional assays to measure receptor activity in heterologous cell systems expressing the rat GALR2 receptor.

Receptor autoradiography

The relative proportion of the total [$^{125}$I]galanin binding attributable to the GALR2 receptor was determined as the binding which was removed by 60 nM [D-Trp$^2$]galanin$_{(1-29)}$. The numerical representations in Table 2 indicate: 1) the relative intensity of the total binding obtained with [$^{125}$I] galanin, with +3 being the maximum; and 2) the relative amount of this binding attributable to GALR2, with +3 again being the maximum.

Total [$^{125}$I]galanin binding was observed in many regions of the rat brain, and was especially intense in the forebrain, including the amygdala, parts of the hypothalamus and thalamus, the septum, and the ventral hippocampus. Other regions with intense binding signals included the superior colliculus, the central gray, and the dorsal horn of the spinal cord. The inclusion of 5 µM porcine galanin in the incubation resulted in a complete displacement of [$^{125}$I]galanin binding from the rat brain tissue sections. The use of 60 nM [D-Trp$^2$]galanin$_{(1-29)}$ partially displaced [$^{125}$I]galanin binding from many regions of the rat brain.

The areas most affected by the GALR2 selective ligand were the lateral septum, the paraventricular hypothalamic nucleus, the centromedial and centrolateral thalamic nuclei, the amygdalopiriform area of the amygdala, and the superior colliculus. Other forebrain regions with lesser but still significant reductions in [$^{125}$I]galanin binding included the piriform and entorhinal cortices, the globus pallidus, the supraoptic, lateral, and ventromedial hypothalamic nuclei, and the anterior, cortical, medial, and central amygdaloid nuclei. In the midbrain, pons and medulla, [D-Trp$^2$]galanin $_{(1-29)}$ partially reduced the total binding in the central gray, the raphe obscurus and raphe magnus, the parabrachial nucleus, the pontine reticular formation, the hypoglossal nucleus, and the gigantocellular reticular nucleus.

In contrast, there were a number of areas in which [D-Trp$^2$]galanin$_{(1-29)}$ had little or no effect on the total [$^{125}$I]galanin binding. Of these, the most striking were the nucleus of the lateral olfactory tract, the ventral hippocampus, and the dorsal horn of the spinal cord. Other areas in which significant binding remained included the olfactory bulb, the insular cortex, the islands of Calleja, the nucleus accumbens, the lateral habenula, the arcuate nucleus, and the spinal trigeminal nucleus.

EXPERIMENTAL DISCUSSION

In order to clone additional members of the galanin receptor family, we designed an expression cloning strategy based on the potential presence of multiple galanin receptors in the hypothalamus. Using this strategy we have isolated a cDNA clone encoding a galanin receptor from rat hypothalamus, termed GALR2, that is distinct from the previously cloned GALR1 receptors.

Transient transfection of the isolated cDNA (K985) encoding GALR2 resulted in high affinity binding of [$^{125}$I]-porcine galanin. The high binding affinity of the GALR2 receptor for galanin$_{(1-29)}$ and its truncated analogs galanin$_{(1-16)}$ and galanin$_{(1-15)}$ strongly supports the notion that the GALR2 receptor is a novel galanin receptor subtype. Both the rat GALR1 and GALR2 receptors seem to bind preferentially to the amino terminus of galanin. Deletion of 13 or 14 amino acids from the carboxyl terminus of galanin still yields peptides with high binding affinity at both the GALR1 and GALR2 receptors. Furthermore, the truncation of the first two amino acids of the amino terminus led to a complete loss of affinity at both GALR1 and GALR2. Consistent with this notion are the findings that the chimeric peptides, which share identical amino acid sequences in the first 12 amino acids with galanin had very similar binding affinities for either GALR1 or GALR2 receptors. In spite of these similarities, the substitution of L-tryptophan with D-tryptophan in position 2 of porcine galanin$_{(1-29)}$, ([D-Trp$^2$]galanin$_{(1-29)}$) led to a 7,000-fold loss in affinity at the GALR1 receptor compared to only a 14-fold reduction at the GALR2 receptor. The same substitution in the truncated analog galanin$_{(1-16)}$ led to a 4,200-fold reduction in affinity at the GALR1 receptor, and only a 6-fold reduction in affinity at the GALR2 receptor. These data suggest that galanin analogs, with modifications at the 2-position, are better tolerated at the GALR2 receptor than at the GALR1 receptor as long as the side chain is an aromatic moiety.

Conversely, the substitution of tyrosine with alanine in position 9 of galanin$_{(1-16)}$, (i.e., to make [Ala]$^9$ galanin) leads to a 680-fold reduction in affinity at the GALR1 receptor and to a 60,000-fold reduction in affinity at the GALR2 receptor. Altogether, the major differences in binding selectivity of the substituted analogs of galanin suggest the existence of substantial differences in the binding domains of these two receptor subtypes.

The existence of such structural differences between the GALR1 and GALR2 receptors are indicative of the potential for the design and discovery of novel subtype selective compounds. In this regard, the expression of the cDNA encoding the rat GALR2 receptors in cultured cell lines provides a unique tool for the discovery of therapeutic agents targeted at galanin receptors.

Localization of galanin receptors

The high affinity of [D-Trp$^2$]galanin$_{(1-29)}$ for the cloned GALR2 receptor (6 nM), and its low affinity for the GALR1 receptor (3 μM), makes it a useful tool for receptor autoradiographic studies. Thus, brain areas in which the total [$^{125}$I]galanin binding is significantly reduced by [D-Trp$^2$] galanin$_{(1-29)}$ are interpreted as areas containing a high proportion of GALR2 receptors. Those with lesser reductions are seen as regions containing a higher concentration of GALR1 receptors. The lateral septum, the paraventricular hypothalamic nucleus, the centromedial and centrolateral thalamic nuclei, the amygdalopiriform area of the amygdala, and the superior colliculus all appear to contain primarily GALR2 receptors. In contrast, the nucleus of the lateral olfactory tract, the ventral hippocampus, and the dorsal horn of the spinal cord appear to contain primarily GALR1 receptors. The predominance of the GALR1 receptor in these regions is consistent with published reports of the GALR1 messenger RNA localization (Parker et al., 1996; Gustafson et al., in press). In most other regions, there appears to be a significant overlap between the two subtypes.

While the functional implications of the GALR2 receptor localization are not well understood at present, there are a number of physiological processes attributable to galanin that could be mediated by this receptor. These include feeding (paraventricular hypothalamic nucleus), cognition (septum and hippocampus), analgesia and/or sensory processing (midline thalamic nuclei), and anxiety and depression (amygdala and hypothalamus).

The observation that galanin is co-released with norepinephrine from sympathetic nerve terminals suggests that galanin could act via galanin receptors in the periphery to modulate nearly every physiological process controlled by sympathetic innervation. Additional therapeutic indications not directly related to localization (supra) include diabetes, hypertension, cardiovascular disorders, regulation of growth hormone release, regulation of fertility, gastric ulcers, gastrointestinal motility/transit/absorption/secretion, glaucoma, inflammation, immune disorders, respiratory disorders (eg. asthma, emphysema).

The physiological and anatomical distribution of galanin-containing neurons suggests potential roles of galanin receptors mediating effects on cognition, analgesia, neuroendocrine regulation, control of insulin release and control of feeding behavior. Of particular relevance to the role of the novel GALR2 receptor, are those functions mediated by galanin receptors in the rat hypothalamus.

Studies in rats indicate that the injection of galanin in the hypothalamus increases food intake (Kyrouli et al, 1990, and Schick et al, 1993) and that this stimulatory effect of galanin is blocked by prior administration of M40 and C7 (Liebowitz and Kim, 1992; and Corwin, 1993). The expression of the mRNA encoding the GALR1 receptor in the rat hypothalamus, (Parker et al., 1996, Gustafson et al., in press) and the fact that the novel GALR2 receptor was cloned from a cDNA library prepared from rat hypothalamus argues in favor of either receptor subtype to be involved in the regulation of feeding behavior (Parker et al., in press). However, the evidence against the involvement of GALR1 in the stimulation of feeding behavior stems from the fact that M40 and C7 are known to be agonists, and not antagonists, in cell lines expressing the cloned human and rat GALR1 receptors (Heuillet et al. 1994; Hale et al. 1993; and Bartfai et al. 1993).

TABLE 1

Binding of galanin peptide analogs to the recombinant rat GALR1 and GALR2 receptors.

| Analog | GALR1 (pKi) | | GALR2 (pKi) | |
| --- | --- | --- | --- | --- |
|  | Mean | SEM* | Mean | SEM |
| porcine galanin$_{(1-29)}$ | 9.34 | 0.15 | 9.35 | 0.14 |
| [D-Trp$^2$]porcine galanin$_{(1-29)}$ | 5.46 | 0.04 | 8.19 | 0.26 |
| [Phe$^2$]porcine galanin$_{(1-29)}$ | 5.99 | 0.13 | 5.64 | 0.11 |
| [D-Ala$^7$]porcine galanin$_{(1-29)}$ | 8.66 | 0.04 | 8.76 | 0.09 |
| galanin$_{(1-16)}$ | 8.66 | 0.01 | 8.76 | 0.13 |
| [D-Trp$^2$]galanin$_{(1-16)}$ | 4.40 | 0.09 | 8.02 | 0.10 |
| [Ala$^5$]galanin$_{(1-16)}$ | 6.27 | 0.05 | 7.46 | 0.13 |
| [Ala$^9$]galanin$_{(1-16)}$ | 5.83 | 0.02 | 3.98 | 0.10 |
| galanin$_{(1-15)}$ | 8.47 | 0.04 | 9.19 | 0.06 |
| [Phe$^2$]galanin$_{(1-15)}$ | 4.63 | 0.03 | 5.85 | 0.49 |

TABLE 1-continued

Binding of galanin peptide analogs to the recombinant rat GALR1 and GALR2 receptors.

| Analog | GALR1 (pKi) Mean | SEM* | GALR2 (pKi) Mean | SEM |
|---|---|---|---|---|
| porcine galanin$_{(3-29)}$ | <4.0 | | <4.0 | |
| galantide | 8.02 | 0.08 | 8.70 | 0.07 |
| C-7 | 7.79 | 0.01 | 7.72 | 0.09 |
| M32 | 9.21 | 0.10 | 9.23 | 0.05 |
| M35 | 9.48 | 0.07 | 9.24 | 0.10 |
| M40 | 8.44 | 0.09 | 9.14 | 0.21 |

*SEM = standard error of the mean, from 3 independent experiments.

TABLE 2

Distribution of [$^{125}$I]galanin binding in rat brain. Total binding is compared to the amount attributable to GalR2 (as indicated by displacement of [$^{125}$I]galanin by 60 nM [D-Trp$^2$]porcine galanin$_{(1-29)}$).

| Region | Total [$^{125}$I]Gal binding | Putative GalR2 sites | Potential Applications |
|---|---|---|---|
| Olfactory bulb | +3 | +1 | Modulation of olfactory sensation |
| Anterior olfactory n. | +3 | +1 | Modulation of olfactory sensation |
| Cortex | | | |
| dorsal neocortex, layer 4 | +1 | +1 | Sensory integration |
| piriform | +2 | +1 | Modulation of olfactory sensation |
| agranular insular | +3 | +1 | Processing of visceral information |
| entorhinal | +2 | +1 | |
| dorsal endopiriform | +2 | +1 | |
| Claustrum | +2 | +1 | Visual processing |
| Basal ganglia | | | |
| n. accumbens | +2 | 0 | Modulation of dopaminergic function |
| olfactory tubercle | +2 | +1 | |
| globus pallidus | +1 | +1 | |
| islands of Calleja | +3 | +1 | |
| Septal area | | | Cognitive enhancement via cholinergic system |
| lateral septum | +3 | +2 | |
| diagonal band n. | +2 | 0 | |
| Hypothalamus | | | |
| anterior | +1 | 0 | Neuroendocrine regulation |
| supraoptic n. | +2 | +1 | |
| paraventricular | +2 | +2 | Appetite/obesity |
| ventromedial | +2 | +1 | |
| arcuate | +1 | 0 | |
| lateral | +2 | +1 | |
| medial mammillary | +2 | +1 | |
| Thalamus | | | Analgesia/sensory modulation |
| paraventricular n. | +1 | 0 | |
| centromedial | +3 | +2 | |
| paracentral | +3 | +1 | |
| rhomboid | +1 | 0 | |
| reuniens | +2 | +1 | |
| mediodorsal | +2 | 0 | |
| reticular n. | +1 | +½ | |
| centrolateral n. | +3 | +2 | |
| zona incerta | +2 | +1 | |
| lateral dorsal | +1 | +½ | |
| habenula | +3 | +1 | Anxiety/sleep disorders |
| Hippocampus | | | Cognition enhancement/ ischaemia |
| Ca1, ventral | +3 | 0 | |
| subiculum | +2 | +1 | |
| Amygdala | | | Anxiolytic, appetite, depression |
| bed n. stria terminalis | +3 | +1 | |

TABLE 2-continued

Distribution of [$^{125}$I]galanin binding in rat brain. Total binding is compared to the amount attributable to GalR2 (as indicated by displacement of [$^{125}$I]galanin by 60 nM [D-Trp$^2$]porcine galanin$_{(1-29)}$).

| Region | Total [$^{125}$I]Gal binding | Putative GalR2 sites | Potential Applications |
|---|---|---|---|
| n. lateral olfactory tract | +3 | 0 | |
| Amygdala | | | Anxiolytic, appetite, depression |
| anterior | +2 | +1 | |
| medial | +3 | +1 | |
| cortical | +2 | +1 | |
| central | +3 | +1 | |
| amygdalohippocampal | +2 | 0 | |
| amygdalopiriform | +3 | +2 | |
| Midbrain | | | |
| superior colliculus | +3 | +2 | Visual function |
| raphe obscurus | +2 | +1 | Analgesia |
| central gray | +2 | +1 | Analgesia |
| Pons/medulla | | | |
| raphe magnus | +2 | +1 | Analgesia |
| parabrachial n. | +2 | +1 | |
| pontine ret. n. | +2 | +1 | |
| reticulotegmental | +2 | +1 | |
| gigantocellular | +2 | +1 | |
| motor trigeminal | +1 | 0 | |
| spinal trigeminal | +3 | +1 | Migraine |
| hypoglossal n. | +2 | +1 | Motor coordination |
| area postrema | +1 | 0 | |
| Spinal cord | | | |
| dorsal horn | +3 | +1 | Analgesia |

TABLE 3

Northern blot hybridization of GALR2 receptor in brain and various peripheral rat tissues.

| Tissue | Blot 1 | Blot 2 | Mean Signal | Therapeutic Indications |
|---|---|---|---|---|
| Heart | +++ | ++ | 2.5 | Cardiovascular Indications (including hypertension and heart failure) |
| Brain | ++++ | ++++ | 4.0 | Obesity/feeding, analgesia, cognition enhancement, Alzheimer's disease, depression, anxiety, sleep disorders, Parkinson's disease, traumatic brain injury, convulsion/epilepsy |
| Spleen | ++ | ++ | 2.0 | Immune functions, hematopoiesis |
| Lung | ++++ | ++++ | 4.0 | Respiratory disorders, asthma, emphysema, lung cancer diagnostics |
| Liver | ++ | − | 1.0 | Diabetes |
| Skeletal Muscle | + | ++ | 1.5 | Diabetes |
| Kidney | +++ | +++ | 3.0 | Hypertension, electrolyte balance, diuretic, anti-diuretic |
| Testis | +++ | + | 2.0 | Reproductive function |

REFERENCES

Ahrén, B. and S. Lindskog (1992) *Int. J. Pancreatol.* 11:147–160.

Amiranoff, B. A. M. Lorinet, and M. Laburthe (1991) *Eur. J. Biochem.* 195:459–463.

Amiranoff, B. A. L. Servin, C. Rouyer-Fessard, A. Couvineau, K. Tatemoto, and M. Laburthe (1987) *Endocrin.* 121:284–289.

Aruffo, A. and B. Seed (1987) *Proc. Natl. Acad. Sci. USA* 84:8573–8577.

Bhathena, S. J., H. K. Oie, A. F. Gazdar, N. R. Voyles, S. D. Wilkins, and L. Recant (1982) *Diabetes* 31:521–531.

Bartfai, T., K. Bedecs, T. Land, Ü. Langel, R. Bertorelli, P. Girotti, S. Consolo, Y.-J. Yu, Z. Weisenfeld-Hallin, S. Nilsson, V. Pieribone, and T. Hökfelt (1991) *Proc. Natl. Acad. Sci. USA* 88:10961–10965.

Bartfai, T., T. Hokfelt, and U. Langel, Crit. Rev. *Neurobiol.* 7:229–274.

Bartfai, T., Ü. Langel, K. Bedecs, S. Andell, T. Land, S. Gregersen, B. Ahren, P. Girotti, S. Consolo, R. Corwin, J. Crawley, X. Xu, Z. Weisenfeld-Hallin, and T. Hökfelt (1993) *Proc. Natl. Acad. Sci. USA* 88:11287–11291.

Bennet, W. M., S. F. Hill, M. A. Ghatei, and S. R. Bloom (1991) *J. Endocrin.* 130:463–467.

Borden, L. A., K. E. Smith., P. R. Hartig, T. A. Branchek, and R. L. Weinshank (1992) *J. Biol. Chem.* 267:21098–21104.

Borden, L. A., K. E. Smith, E. L. Gustafson, T. A. Branchek, and R. L. Weinshank (1994) *J. Neurochem.* In Press.

Boyle, M. R., C. B. Verchere, G. McKnight, S. Mathews, K. Walker, and G. J. Taborsky, Jr. (1994) *Reg. Peptides* 50:1–11.

Bradford, M. M. (1976). A rapid and sensitive method for the quantitation of microgram quantities of protein utilizing the principle of protein-dye binding. *Anal. Biochem.* 72:248–254.

Burbach, J. P. and O. C. Meijer (1992) *Eur. J. Pharmacol.* 227:1–18.

Burgevin, M.-C., Loquet, I., Quarteronet, D., and Habert-Ortoli, E. (1995) *J. Molec. Neurosci.,* 6:33–41.

Bush, A. W., Borden, L. A., Greene, L. A., and Maxfield, F. R. (1991) *J. Neurochem.* 57:562–574.

Chan-Palay, V. (1988) *J. Comp. Neurol.* 273:543–557. Chen, Y., A. Fournier, A. Couvineau, M. Laburthe, and B. Amiranoff (1993) *Proc. Natl. Acad. Sci. USA* 90:3845–3849.

Chirgwin, J. M., A. E. Przybyla, R. J. MacDonald, and W. J. Rutter. (1979) *Biochemistry* 18:5294–5299.

Consolo, S., R. Bertorelli, P. Girotti, C. La Porta, T. Bartfai, M. Parenti, and M. Zambelli (1991) *Neurosci. Lett.* 126:29–32.

Crawley, J. N. (1993) *Behav. Brain Res.* 57:133–141.

Crawley, J. N., J. K. Robinson, Ü. Langel, and T. Bartfai (1993) *Brain. Res.* 600:268–272.

Cullen, B. (1987). Use of eurkaryotic expression technology in the functional analysis of cloned genes. *Methods Enzymol.* 152:685–704.

D'Andrea, A. D., H. F. Lodish, and G. W. Gordon (1989) *Cell* 57:277–285.

Fisone, G., C. F. Wu, S. Consolo, Ö. Nördstrom, N. Brynne, T. Bartfai, T. Melander, T. Hökfelt (1987) *Proc. Natl. Acad. Sci USA* 84:7339.

Gearing, D. P., King, J. A., Gough, N. M. and Nicola N. A. (1989) *EMBO J.* 8:3667–3676.

Gerald, C., M. Walker, T. Branchek, and R. Weinshank (1994) DNA Encoding a Human Neuropeptide Y/Peptide YY (Y2) Receptor and Uses Thereof, U.S. patent application Ser. No. 08/192,288, filed Feb. 3, 1994.

Gillison, S. L., and W. G. Sharp (1994) *Diabetes* 43:24–32. Gregersen, S., S. Lindskog, T. Land, U. Langel, T. Bartfai, and B. Ahren (1993) *Eur J. Pharmacol.* 232:35–39.

Gu, Z.-F., W. J. Rossowski, D. H. Coy, T. K. Pradhan, and R. T. Jensen (1993) *J. Phamacol. Exper. Ther.* 266:912–918.

Gu, Z.-F., Pradhan, T. K., Coy, D. H., and Jensen, R. T. (1995) *J. Pharmacol. Exp. Ther.,* 272:371–378.

Gubler, U abd B. J. Hoffman. (1983). A simple and very efficient method for generating cDNA libraries. *Gene.* 25, 263–269

Gustafson, E. L., Smith, K. E., Durkin, M. M., Gerald, C., and Branchek, T. A. (1996) *Neuroreport,* in press.

Habert-Ortoli, E., Amiranoff, B., Loquet, I., Laburthe, M., and J.-F. Mayaux (1994) *Proc. Natl. Acad. Sci. USA* 91:9780–9783.

Hedlund, P. B., N. Yanaihara, and K. Fuxe (1992) *Eur. J. Pharm.* 224:203–205.

Heuillet, E., Bouaiche, Z., Menager, J., Dugay, P., Munoz, N., Dubois, H., Amiranoff, B., Crespo, A., Lavayre, J., Blanchard, J.-C., and Doble, A. (1994) *Eur. J. Pharmacol.,* 269:139–147.

Kaplan, L. M., S. M. Gabriel, J. I. Koenig, M. E. Sunday, E. R. Spindel, J. B. Martin, and W. W. Chin (1988) *Proc. Natl. Acad. Sci. USA* 85:7408–7412.

Kieffer, B., Befort, K., Gaveriaux-Ruff, C. and Hirth, C. G. (1992). The δ-opioid receptor:Isolation of a cDNA by expression cloning and pharmacological characterization. *Proc. Natl. Acad. Sci. USA* 89:12048–12052.

Kluxen, F. W., Bruns, C. and Lubbert H. (1992). Expression cloning of a rat brain somatostatin receptor cDNA. *Proc. Natl. Acad. Sci. USA* 89:4618–4622.

Kornfeld, R. and Kornfeld, S. (1985). Assembly of asparagine linked oligosaccharides. *Annu. Rev. Biochem.* 54:631–664.

Kozak, M. (1989). The scanning model for translation: an update. *J. Cell Biol.* 108:229–241.

Kozak, M. (1991). Structural features in eukaryotic mRNAs that modulate the initiation of translation. *J. Biol. Chem.* 266:19867–19870.

Kyrkouli, S. E., B. G. Stanley, R. D. Seirafi and S. F. Leibowitz (1990) *Peptides* 11:995–1001.

Lagny-Pourmir, I., A. M. Lorinet, N. Yanaihara, and M. Laburthe (1989) *Peptides* 10:757–761.

Landschultz, W. H., Johnson, P. F. and S. L. McKnight. (1988). The leucine zipper: a hypothetical structure common to a new class of DNA binding proteins. *Science* 240:1759–1764.

Leibowitz, S. F. and T. Kim (1992) *Brain Res.* 599:148–152.

Maggio, R., Vogel Z. and J. Wess. (1993). Coexpression studies with mutant muscarinic/adrenergic receptors provide evidence for intermolecular "cross-talk" between G-protein-linked receptors. *Proc. Natl. Acad. Sci. USA* 90:3103–3107.

McCormick, M. (1987). Sib Selection. *Methods in Enzymoloay,* 151:445–449.

Melander, T., C. Köhler, S. Nilsson, T. Hökfelt, E. Brodin, E. Theodorsson, and T. Bartfai (1988) *J. Chem. Neuroanat.* 1:213–233.

Merchenthaler, I., F. J. López, and A. Negro-Vilar (1993) *Prog. Neurobiol.* 40:711–769.

Miller, J. and Germain, R. N. (1986). Efficient cell surface expression of class II MHC molecules in the absence of associated invariant chain. *J. Exp. Med.* 164: 1478–1489.

Ögren, S.-O., T. Hökfelt, K. Kask, Ü. Langel, and T. Bartfai (1992) *Neurosci.* 51:1.

Palazzi, E., G. Fisone, T. Hokfelt, T. Bartfai, and S. Consolo (1988) *Eur. J. Pharmacol.* 148:479.

Parker, E. M., Izzarelli, D., Nowak, H., Mahle, C., Iben, L., Wang, J., and Goldstein, M. E. (1996) *Mol. Brain Res.,* 34:179–189.

Post, C., L. Alari, and T. Hokfelt (1988) *Acta Physiol. Scand.* 132:583.

Probst, W. C., Snyder, L. A., Schuster, D. I., Brosius, J and Sealfon, S. C. (1992). Sequence alignment of the G-protein coupled receptor superfamily. *DNA and Cell Bio.* 11:1–20.

Sanger, S. (1977) *Proc. Natl. Acad. Sci. USA* 74:5463–5467.

Servin, A. L., B. Amiranoff, C. Rouyer-Fessard, K. Tatemoto, and M. Laburthe (1987) *Biochem. Biophys. Res. Comm.* 144:298–306.

Shen,Y., Monsma, F. J. Jr., Metcalf, M. A., Jose, P. A., Hamblin, M. W., and Sibley, D. R. (1993Molecular Cloning and Expression of a 5-Hydroxytryptamine$_7$ Serotonin Receptor Subtype. *J. Biol. Chem.* 268:18200–18204.

Sims, J. E., C. J. March, D. Cosman, M. B. Widmer, H. R. Macdonald, C. J. McMahan, C. E. Grubin, J. M. Wignal, J. L. Jackson, S. M. Call, D. Freind, A. R. Alpert, S. Gillis, D. L. Urdal, and S. K. Dower (1988) *Science* 241:585–588.

Skofitsch, G. and D. M. Jacobowitz (1985) *Peptides* 6:509–546.

Skofitsch, G., M. A. Sills, and D. M. Jacobowitz (1986) *Peptides* 7:1029–1042.

Smith, K. E., L. A. Borden, P. R. Hartig, T. Branchek, and R. L. Weinshank (1992) *Neuron* 8:927–935.

Smith, K. E., L. A. Borden, C-H. D. Wang, P. R. Hartig, T. A. Branchek, and R. L. Weinshank (1992a) *Mol. Pharmacol.* 42:563–569.

Smith, K. E., S. G. Fried, M. M. Durkin, E. L. Gustafson, L. A. Borden, T. A. Branchek, and R. L. Weinshank (1994) *FEBS Letters,* In press.

Sundström, E., T. Archer, T. Melander, and T. Hökfelt (1988) *Neurosci. Lett.* 88:331.

Tempel, D. L., K. J. Leibowitz, and S. F. Leibowitz (1988) *Peptides* 9:300–314.

Vrontakis, M. E., L. M. Peden, M. L Duckworth, and H. G. Friesen (1987) *J. Biol. Chem.* 262:16755–16760.

Warden, D. and H. V. Thorne. (1968). Infectivity of polyoma virus DNA for mouse embryo cells in presence of diethylaminoethyl-dextran. *J. Gen. Virol.* 3:371.

Wiesenfeld-Hallin, Z., X. J. Xu, J. X. Hao, and T. Hokfelt (1993) *Acta Physiol. Scand.* 147:457–458.

Wiesenfeld-Hallin, Z., et al. (1992) *Proc. Natl. Acad. Sci. USA* 89:3334–3337.

Wynick D., D. M. Smith, M. Ghatei, K. Akinsanya, R. Bhogal, P. Purkiss, P. Byfield, N. Yanaihara, and S. R. Bloom (1993) *Proc. Natl. Acad. Sci. USA* 90:4231–4245.0

---

What is claimed is:

1. A process for identifying a chemical compound which specifically binds to a galanin receptor (GALR2), which comprises contacting nonneuronal cells transfected with DNA encoding, and expressing on their cell surface, a rat galanin receptor (GALR2), wherein the rat galanin receptor (GALR2) has an amino acid sequence as shown in SEQ ID NO: 8, with the chemical compound under conditions suitable for binding, and detecting specific binding of the chemical compound to the galanin receptor (GALR2).

2. A process involving competitive binding for identifying a chemical compound which specifically binds to a galanin receptor (GALR2) which comprises separately contacting nonneuronal cells transfected with DNA encoding, and expressing on their cell surface, a rat galanin receptor (GALR2), wherein the rat galanin receptor (GALR2) has an amino acid sequence as shown in SEQ ID NO: 8, with both the chemical compound and a second chemical compound known to bind to the receptor, and with only the second chemical compound, under conditions suitable for binding of both compounds, and detecting specific binding of the chemical compound to the galanin receptor (GALR2), a decrease in the binding of the second chemical compound to the galanin receptor (GALR2) in the presence of the chemical compound indicating that the chemical compound binds to the galanin receptor (GALR2).

3. The process of claim 1, or 2, wherein the nonneuronal cell is a mammalian cell or an insect cell.

4. The process of claim 3, wherein the mammalian cell is a COS-7 cell, a 293 human embryonic kidney cell, a NIH 3T3 cell, or a LM(tk-) cell.

5. The process of claim 4, wherein the LM(tk-) cell is designated L-rGALR2-8 (ATCC Accession NO. CRL-12074).

6. The process of claim 1 wherein the insect cell is a SF9 or a Sf21 cell.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

TGGGCAACAG CCTAGTGATC ACCG      24

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

CTGCTCCCAG CAGAAGGTCT GGTT      24

(2) INFORMATION FOR SEQ ID NO:3:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:3:

CCTCAGTGAA GGGAATGGGA GCGA      24

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

```
CTCATTGCAA ACACGGCACT TGAACA                                              26
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
CTTGCTTGTA CGCCTTCCGG AAGT                                                24
```

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
GAGAACTTCA TCACGCTGGT GGTG                                                24
```

(2) INFORMATION FOR SEQ ID NO:7:

(i) SEQUENCE CHARACTERISTICS:
        (A) LENGTH: 1119 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..1119

(xi) SEQUENCE DESCRIPTION: SEQ ID NO:7:

```
ATG AAT GGC TCC GGC AGC CAG GGC GCG GAG AAC ACG AGC CAG GAA GGC            48
Met Asn Gly Ser Gly Ser Gln Gly Ala Glu Asn Thr Ser Gln Glu Gly
 1               5                  10                  15

GGT AGC GGC GGC TGG CAG CCT GAG GCG GTC CTT GTA CCC CTA TTT TTC            96
Gly Ser Gly Gly Trp Gln Pro Glu Ala Val Leu Val Pro Leu Phe Phe
             20                  25                  30

GCG CTC ATC TTC CTC GTG GGC ACC GTG GGC AAC GCG CTG GTG CTG GCG           144
Ala Leu Ile Phe Leu Val Gly Thr Val Gly Asn Ala Leu Val Leu Ala
         35                  40                  45

GTG CTG CTG CGC GGC GGC CAG GCG GTC AGC ACC ACC AAC CTG TTC ATC           192
Val Leu Leu Arg Gly Gly Gln Ala Val Ser Thr Thr Asn Leu Phe Ile
     50                  55                  60

CTC AAC CTG GGC GTG GCC GAC CTG TGT TTC ATC CTG TGC TGC GTG CCT           240
Leu Asn Leu Gly Val Ala Asp Leu Cys Phe Ile Leu Cys Cys Val Pro
 65                  70                  75                  80
```

```
TTC CAG GCC ACC ATC TAC ACC CTG GAC GAC TGG GTG TTC GGC TCG CTG      288
Phe Gln Ala Thr Ile Tyr Thr Leu Asp Asp Trp Val Phe Gly Ser Leu
             85                  90                  95

CTC TGC AAG GCT GTT CAT TTC CTC ATC TTT CTC ACT ATG CAC GCC AGC      336
Leu Cys Lys Ala Val His Phe Leu Ile Phe Leu Thr Met His Ala Ser
            100                 105                 110

AGC TTC ACG CTG GCC GCC GTC TCC CTG GAC AGG TAT CTG GCC ATC CGC      384
Ser Phe Thr Leu Ala Ala Val Ser Leu Asp Arg Tyr Leu Ala Ile Arg
            115                 120                 125

TAC CCG CTG CAC TCC CGA GAG TTG CGC ACA CCT CGA AAC GCG CTG GCC      432
Tyr Pro Leu His Ser Arg Glu Leu Arg Thr Pro Arg Asn Ala Leu Ala
        130                 135                 140

GCC ATC GGG CTC ATC TGG GGG CTA GCA CTG CTC TTC TCC GGG CCC TAC      480
Ala Ile Gly Leu Ile Trp Gly Leu Ala Leu Leu Phe Ser Gly Pro Tyr
145             150                 155                 160

CTG AGC TAC TAC CGT CAG TCG CAG CTG GCC AAC CTG ACA GTA TGC CAC      528
Leu Ser Tyr Tyr Arg Gln Ser Gln Leu Ala Asn Leu Thr Val Cys His
            165                 170                 175

CCA GCA TGG AGC GCA CCT CGA CGT CGA GCC ATG GAC CTC TGC ACC TTC      576
Pro Ala Trp Ser Ala Pro Arg Arg Arg Ala Met Asp Leu Cys Thr Phe
            180                 185                 190

GTC TTT AGC TAC CTG CTG CCA GTG CTA GTC CTC AGT CTG ACC TAT GCG      624
Val Phe Ser Tyr Leu Leu Pro Val Leu Val Leu Ser Leu Thr Tyr Ala
            195                 200                 205

CGT ACC CTG CGC TAC CTC TGG CGC ACA GTC GAC CCG GTG ACT GCA GGC      672
Arg Thr Leu Arg Tyr Leu Trp Arg Thr Val Asp Pro Val Thr Ala Gly
        210                 215                 220

TCA GGT TCC CAG CGC GCC AAA CGC AAG GTG ACA CGG ATG ATC ATC ATC      720
Ser Gly Ser Gln Arg Ala Lys Arg Lys Val Thr Arg Met Ile Ile Ile
225             230                 235                 240

GTG GCG GTG CTT TTC TGC CTC TGT TGG ATG CCC CAC CAC GCG CTT ATC      768
Val Ala Val Leu Phe Cys Leu Cys Trp Met Pro His His Ala Leu Ile
            245                 250                 255

CTC TGC GTG TGG TTT GGT CGC TTC CCG CTC ACG CGT GCC ACT TAC GCG      816
Leu Cys Val Trp Phe Gly Arg Phe Pro Leu Thr Arg Ala Thr Tyr Ala
            260                 265                 270

TTG CGC ATC CTT TCA CAC CTA GTT TCC TAT GCC AAC TCC TGT GTC AAC      864
Leu Arg Ile Leu Ser His Leu Val Ser Tyr Ala Asn Ser Cys Val Asn
        275                 280                 285

CCC ATC GTT TAC GCT CTG GTC TCC AAG CAT TTC CGT AAA GGT TTC CGC      912
Pro Ile Val Tyr Ala Leu Val Ser Lys His Phe Arg Lys Gly Phe Arg
        290                 295                 300

AAA ATC TGC GCG GGC CTG CTG CGC CCT GCC CCG AGG CGA GCT TCG GGC      960
Lys Ile Cys Ala Gly Leu Leu Arg Pro Ala Pro Arg Arg Ala Ser Gly
305                 310                 315                 320

CGA GTG AGC ATC CTG GCG CCT GGG AAC CAT AGT GGC AGC ATG CTG GAA     1008
Arg Val Ser Ile Leu Ala Pro Gly Asn His Ser Gly Ser Met Leu Glu
            325                 330                 335

CAG GAA TCC ACA GAC CTG ACA CAG GTG AGC GAG GCA GCC GGG CCC CTT     1056
Gln Glu Ser Thr Asp Leu Thr Gln Val Ser Glu Ala Ala Gly Pro Leu
        340                 345                 350

GTC CCA CCA CCC GCA CTT CCC AAC TGC ACA GCC TCG AGT AGA ACC CTG     1104
Val Pro Pro Pro Ala Leu Pro Asn Cys Thr Ala Ser Ser Arg Thr Leu
        355                 360                 365

GAT CCG GCT TGT TAA                                                 1119
Asp Pro Ala Cys *
    370
```

(2) INFORMATION FOR SEQ ID NO:8:

(i) SEQUENCE CHARACTERISTICS:

(A) LENGTH: 372 amino acids
(B) TYPE: amino acid
(D) TOPOLOGY: linear (ii) MOLECULE TYPE: protein (xi) SEQUENCE DESCRIPTION: SEQ ID NO:8:

```
Met Asn Gly Ser Gly Ser Gln Gly Ala Glu Asn Thr Ser Gln Glu Gly
 1               5                  10                  15

Gly Ser Gly Gly Trp Gln Pro Glu Ala Val Leu Val Pro Leu Phe Phe
                20                  25                  30

Ala Leu Ile Phe Leu Val Gly Thr Val Gly Asn Ala Leu Val Leu Ala
                35                  40                  45

Val Leu Leu Arg Gly Gly Gln Ala Val Ser Thr Thr Asn Leu Phe Ile
 50                  55                  60

Leu Asn Leu Gly Val Ala Asp Leu Cys Phe Ile Leu Cys Cys Val Pro
 65                  70                  75                  80

Phe Gln Ala Thr Ile Tyr Thr Leu Asp Asp Trp Val Phe Gly Ser Leu
                85                  90                  95

Leu Cys Lys Ala Val His Phe Leu Ile Phe Leu Thr Met His Ala Ser
                100                 105                 110

Ser Phe Thr Leu Ala Ala Val Ser Leu Asp Arg Tyr Leu Ala Ile Arg
                115                 120                 125

Tyr Pro Leu His Ser Arg Glu Leu Arg Thr Pro Arg Asn Ala Leu Ala
 130                 135                 140

Ala Ile Gly Leu Ile Trp Gly Leu Ala Leu Leu Phe Ser Gly Pro Tyr
 145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Ala Met Asp Leu Cys Thr Phe
                180                 185                 190

Val Phe Ser Tyr Leu Leu Pro Val Leu Val Leu Ser Leu Thr Tyr Ala
                195                 200                 205

Arg Thr Leu Arg Tyr Leu Trp Arg Thr Val Asp Pro Val Thr Ala Gly
 210                 215                 220

Ser Gly Ser Gln Arg Ala Lys Arg Lys Val Thr Arg Met Ile Ile Ile
225                 230                 235                 240

Val Ala Val Leu Phe Cys Leu Cys Trp Met Pro His His Ala Leu Ile
                245                 250                 255

Leu Cys Val Trp Phe Gly Arg Phe Pro Leu Thr Arg Ala Thr Tyr Ala
                260                 265                 270

Leu Arg Ile Leu Ser His Leu Val Ser Tyr Ala Asn Ser Cys Val Asn
                275                 280                 285

Pro Ile Val Tyr Ala Leu Val Ser Lys His Phe Arg Lys Gly Phe Arg
 290                 295                 300

Lys Ile Cys Ala Gly Leu Leu Arg Pro Ala Pro Arg Arg Ala Ser Gly
305                 310                 315                 320

Arg Val Ser Ile Leu Ala Pro Gly Asn His Ser Gly Ser Met Leu Glu
                325                 330                 335

Gln Glu Ser Thr Asp Leu Thr Gln Val Ser Glu Ala Ala Gly Pro Leu
                340                 345                 350

Val Pro Pro Pro Ala Leu Pro Asn Cys Thr Ala Ser Ser Arg Thr Leu
                355                 360                 365

Asp Pro Ala Cys   *
 370
```

(2) INFORMATION FOR SEQ ID NO:9:

(i) SEQUENCE CHARACTERISTICS:
        (A) LENGTH: 2200 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 46..414

(ix) FEATURE:
        (A) NAME/KEY: CDS
        (B) LOCATION: 1422..2171

(xi) SEQUENCE DESCRIPTION: SEQ ID NO:9:

```
CAAGACCCGG ACAGCTGCGG GAGCGGCGTC CACTTTGGTG ATACC ATG AAT GGC          54
                                                 Met Asn Gly
                                                   1

TCC GGC AGC CAG GGC GCG GAG AAC ACG AGC CAG GAA GGC GGT AGC GGC       102
Ser Gly Ser Gln Gly Ala Glu Asn Thr Ser Gln Glu Gly Gly Ser Gly
      5                  10                  15

GGC TGG CAG CCT GAG GCG GTC CTT GTA CCC CTA TTT TTC GCG CTC ATC       150
Gly Trp Gln Pro Glu Ala Val Leu Val Pro Leu Phe Phe Ala Leu Ile
 20                  25                  30                  35

TTC CTC GTG GGC ACC GTG GGC AAC GCG CTG GTG CTG GCG GTG CTG CTG       198
Phe Leu Val Gly Thr Val Gly Asn Ala Leu Val Leu Ala Val Leu Leu
                 40                  45                  50

CGC GGC GGC CAG GCG GTC AGC ACC ACC AAC CTG TTC ATC CTC AAC CTG       246
Arg Gly Gly Gln Ala Val Ser Thr Thr Asn Leu Phe Ile Leu Asn Leu
             55                  60                  65

GGC GTG GCC GAC CTG TGT TTC ATC CTG TGC TGC GTG CCT TTC CAG GCC       294
Gly Val Ala Asp Leu Cys Phe Ile Leu Cys Cys Val Pro Phe Gln Ala
         70                  75                  80

ACC ATC TAC ACC CTG GAC GAC TGG GTG TTC GGC TCG CTG CTC TGC AAG       342
Thr Ile Tyr Thr Leu Asp Asp Trp Val Phe Gly Ser Leu Leu Cys Lys
     85                  90                  95

GCT GTT CAT TTC CTC ATC TTT CTC ACT ATG CAC GCC AGC AGC TTC ACG       390
Ala Val His Phe Leu Ile Phe Leu Thr Met His Ala Ser Ser Phe Thr
100                 105                 110                 115

CTG GCC GCC GTC TCC CTG GAC AGG TGAGTGAACA TCGGAGAACT ATTGTATCTG      444
Leu Ala Ala Val Ser Leu Asp Arg
                120

AGATAGGGGC TTGGGCTGGA GTCACTACAC AGGGGATCCA GAAGGCATGA GCAGAATGGG     504

CGAGAACACT GAAATTACAA AGTGGCCTGA GGCCGTGAAA CGCAAGGGGG AGGGAGATTA     564

AGACTCAGTG ACTGAGAGTG TCTAAGTCGA TGGGAGAAAT CGGGTCTCTG GGGTCCTCGC     624

ATTATTACTG CTTGAGTTAA ATGTCTCTGT GAAACATTGC AGTTCTCAGG CCAGAGTTGG     684

CAGGAAAAGT AACTCGCCAG TGTTCAGATG CTGTTTGAGA GCTGCAGAGA AGCATCTGCT     744

TCTTAGCACC AAGCTCAGCA CCTGGGGCGT TGTCCGGCGC CTTAGGCTTA GGACTGGGCT     804

GTGCTGTGTT AAGACCCATG CTCAAGTCCA ACGGAGTGTA AGCGAGGGCT CCTAGCTGAC     864

ACCCAGAGCC CTCCAGGCCA AGGCTCCCCT CACCGAGATG CCAGCGGTTT TATGCTCCTT     924

CCATAGGTAA AGGACCCAGA AAGAAACATC CAGTATGCCC GGAGGGATCT TGACTGGAAA     984

AGACTGAATC CTGGTCTGGT GACCTTAGTT CCCTGCCCTT TCACATCACT TGGACATTCC    1044

CACAGAAGAG CGGTGAAGAG GCGGTGGTCC TTATTCTCCT CTGGTTTCCA CTGAGTGCAA    1104

CATGTGCGTC CTGAGTACGC TGGAGGGACT CACAAAATTT CAGCTTTCTT TAGGAGTTTC    1164
```

```
CTTGCTGTAG TTTGACCCAA GTCTTCTCCA GGTTTCTGTC AGAACCTCAG GCATGAGGGA      1224

TCTGCCTCCC CTGGTTGTCA CCAGAGGATA ACAATCACTG CCCCCAGAAA TCCAGACAGA      1284

TTCTACAACT TTTAGTCTTC GGTGTTTTGG GGGTGCCCCT TCACGTGGAG TAGGTCGGTG      1344

GCCACATTCC CAGGAGTGAC AATAGCCTAG CAGTGAATCC TCTCGCTTAG CTGATGCCCC      1404

CCCACTGTCC CCACAGG TAT CTG GCC ATC CGC TAC CCG CTG CAC TCC CGA         1454
                   Tyr Leu Ala Ile Arg Tyr Pro Leu His Ser Arg
                    1               5                  10

GAG TTG CGC ACA CCT CGA AAC GCG CTG GCC GCC ATC GGG CTC ATC TGG        1502
Glu Leu Arg Thr Pro Arg Asn Ala Leu Ala Ala Ile Gly Leu Ile Trp
            15                  20                  25

GGG CTA GCA CTG CTC TTC TCC GGG CCC TAC CTG AGC TAC TAC CGT CAG        1550
Gly Leu Ala Leu Leu Phe Ser Gly Pro Tyr Leu Ser Tyr Tyr Arg Gln
        30                  35                  40

TCG CAG CTG GCC AAC CTG ACA GTA TGC CAC CCA GCA TGG AGC GCA CCT        1598
Ser Gln Leu Ala Asn Leu Thr Val Cys His Pro Ala Trp Ser Ala Pro
    45                  50                  55

CGA CGT CGA GCC ATG GAC CTC TGC ACC TTC GTC TTT AGC TAC CTG CTG        1646
Arg Arg Arg Ala Met Asp Leu Cys Thr Phe Val Phe Ser Tyr Leu Leu
60                  65                  70                  75

CCA GTG CTA GTC CTC AGT CTG ACC TAT GCG CGT ACC CTG CGC TAC CTC        1694
Pro Val Leu Val Leu Ser Leu Thr Tyr Ala Arg Thr Leu Arg Tyr Leu
                80                  85                  90

TGG CGC ACA GTC GAC CCG GTG ACT GCA GGC TCA GGT TCC CAG CGC GCC        1742
Trp Arg Thr Val Asp Pro Val Thr Ala Gly Ser Gly Ser Gln Arg Ala
            95                  100                 105

AAA CGC AAG GTG ACA CGG ATG ATC ATC ATC GTG GCG GTG CTT TTC TGC        1790
Lys Arg Lys Val Thr Arg Met Ile Ile Ile Val Ala Val Leu Phe Cys
        110                 115                 120

CTC TGT TGG ATG CCC CAC CAC GCG CTT ATC CTC TGC GTG TGG TTT GGT        1838
Leu Cys Trp Met Pro His His Ala Leu Ile Leu Cys Val Trp Phe Gly
    125                 130                 135

CGC TTC CCG CTC ACG CGT GCC ACT TAC GCG TTG CGC ATC CTT TCA CAC        1886
Arg Phe Pro Leu Thr Arg Ala Thr Tyr Ala Leu Arg Ile Leu Ser His
140                 145                 150                 155

CTA GTT TCC TAT GCC AAC TCC TGT GTC AAC CCC ATC GTT TAC GCT CTG        1934
Leu Val Ser Tyr Ala Asn Ser Cys Val Asn Pro Ile Val Tyr Ala Leu
                160                 165                 170

GTC TCC AAG CAT TTC CGT AAA GGT TTC CGC AAA ATC TGC GCG GGC CTG        1982
Val Ser Lys His Phe Arg Lys Gly Phe Arg Lys Ile Cys Ala Gly Leu
            175                 180                 185

CTG CGC CCT GCC CCG AGG CGA GCT TCG GGC CGA GTG AGC ATC CTG GCG        2030
Leu Arg Pro Ala Pro Arg Arg Ala Ser Gly Arg Val Ser Ile Leu Ala
        190                 195                 200

CCT GGG AAC CAT AGT GGC AGC ATG CTG GAA CAG GAA TCC ACA GAC CTG        2078
Pro Gly Asn His Ser Gly Ser Met Leu Glu Gln Glu Ser Thr Asp Leu
    205                 210                 215

ACA CAG GTG AGC GAG GCA GCC GGG CCC CTT GTC CCA CCA CCC GCA CTT        2126
Thr Gln Val Ser Glu Ala Ala Gly Pro Leu Val Pro Pro Pro Ala Leu
220                 225                 230                 235

CCC AAC TGC ACA GCC TCG AGT AGA ACC CTG GAT CCG GCT TGT TAA            2171
Pro Asn Cys Thr Ala Ser Ser Arg Thr Leu Asp Pro Ala Cys  *
                240                 245                 250

AGGACCAAAG GGCATCTAAC AGCTTCTAG                                        2200

(2) INFORMATION FOR SEQ ID NO:10:

(i) SEQUENCE CHARACTERISTICS:
        (A) LENGTH: 123 amino acids
```

(B) TYPE: amino acid
(D) TOPOLOGY: linear (ii) MOLECULE TYPE: protein (xi) SEQUENCE DESCRIPTION: SEQ ID NO:10:

```
Met Asn Gly Ser Gly Ser Gln Gly Ala Glu Asn Thr Ser Gln Glu Gly
 1               5                  10                  15

Gly Ser Gly Gly Trp Gln Pro Glu Ala Val Leu Val Pro Leu Phe Phe
            20                  25                  30

Ala Leu Ile Phe Leu Val Gly Thr Val Gly Asn Ala Leu Val Leu Ala
        35                  40                  45

Val Leu Leu Arg Gly Gly Gln Ala Val Ser Thr Thr Asn Leu Phe Ile
50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Asp Trp Val Phe Gly Ser Leu
                85                  90                  95

Leu Cys Lys Ala Val His Phe Leu Ile Phe Leu Thr Met His Ala Ser
            100                 105                 110

Ser Phe Thr Leu Ala Ala Val Ser Leu Asp Arg
            115                 120
```

(2) INFORMATION FOR SEQ ID NO:11:

(i) SEQUENCE CHARACTERISTICS:
(A) LENGTH: 249 amino acids
(B) TYPE: amino acid
(D) TOPOLOGY: linear (ii) MOLECULE TYPE: protein (xi) SEQUENCE DESCRIPTION: SEQ ID NO:11:

```
Tyr Leu Ala Ile Arg Tyr Pro Leu His Ser Arg Glu Leu Arg Thr Pro
 1               5                  10                  15

Arg Asn Ala Leu Ala Ala Ile Gly Leu Ile Trp Gly Leu Ala Leu Leu
            20                  25                  30

Phe Ser Gly Pro Tyr Leu Ser Tyr Tyr Arg Gln Ser Gln Leu Ala Asn
        35                  40                  45

Leu Thr Val Cys His Pro Ala Trp Ser Ala Pro Arg Arg Arg Ala Met
50                  55                  60

Asp Leu Cys Thr Phe Val Phe Ser Tyr Leu Leu Pro Val Leu Val Leu
65                  70                  75                  80

Ser Leu Thr Tyr Ala Arg Thr Leu Arg Tyr Leu Trp Arg Thr Val Asp
            85                  90                  95

Pro Val Thr Ala Gly Ser Gly Ser Gln Arg Ala Lys Arg Lys Val Thr
            100                 105                 110

Arg Met Ile Ile Ile Val Ala Val Leu Phe Cys Leu Cys Trp Met Pro
        115                 120                 125

His His Ala Leu Ile Leu Cys Val Trp Phe Gly Arg Phe Pro Leu Thr
    130                 135                 140

Arg Ala Thr Tyr Ala Leu Arg Ile Leu Ser His Leu Val Ser Tyr Ala
145                 150                 155                 160

Asn Ser Cys Val Asn Pro Ile Val Tyr Ala Leu Val Ser Lys His Phe
                165                 170                 175

Arg Lys Gly Phe Arg Lys Ile Cys Ala Gly Leu Leu Arg Pro Ala Pro
            180                 185                 190
```

```
Arg Arg Ala Ser Gly Arg Val Ser Ile Leu Ala Pro Gly Asn His Ser
        195                 200                 205

Gly Ser Met Leu Glu Gln Glu Ser Thr Asp Leu Thr Gln Val Ser Glu
        210                 215                 220

Ala Ala Gly Pro Leu Val Pro Pro Pro Ala Leu Pro Asn Cys Thr Ala
225                 230                     235                 240

Ser Ser Arg Thr Leu Asp Pro Ala Cys  *
                245                 250

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

CAAGGCTGTT CATTTCCTCA TCTTTC                                                26

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

TTGGAGACCA GAGCGTAAAC GATGG                                                 25

(2) INFORMATION FOR SEQ ID NO:14:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

AGTCGACCCG GTGACTGCAG GCTCAGGTTC CCAGCGCGCC AAACG                           45
```